(12) United States Patent
Ra et al.

(10) Patent No.: US 9,211,306 B2
(45) Date of Patent: Dec. 15, 2015

(54) CELLULAR THERAPEUTIC AGENT FOR INCONTINENCE OR URINE COMPRISING STEM CELLS ORIGINATED FROM DECIDUA OR ADIPOSE

(71) Applicant: RNL BIO CO., LTD., Seoul (KR)

(72) Inventors: Jeong Chan Ra, Gyeonggi-do (KR); Hang Young Lee, Gyeonggi-do (KR); Jung Youn Jo, Seoul (KR); Yun Jung Kim, Seoul (KR)

(73) Assignee: RNL BIO CO., LTD., Seoul (KR)

( * ) Notice: Subject to any disclaimer, the term of this patent is extended or adjusted under 35 U.S.C. 154(b) by 459 days.

(21) Appl. No.: 13/738,479

(22) Filed: Jan. 10, 2013

(65) Prior Publication Data

US 2013/0189232 A1    Jul. 25, 2013

Related U.S. Application Data

(63) Continuation of application No. 12/668,592, filed on Nov. 22, 2010, now abandoned.

(30) Foreign Application Priority Data

Nov. 30, 2007   (KR) .................... 10-2007-0124010

(51) Int. Cl.
```
A01N 63/00      (2006.01)
A61K 35/28      (2015.01)
A61K 9/00       (2006.01)
A61K 35/50      (2015.01)
C12N 5/073      (2010.01)
C12N 5/0775     (2010.01)
A61K 35/12      (2015.01)
```

(52) U.S. Cl.
CPC ............... *A61K 35/28* (2013.01); *A61K 9/0019* (2013.01); *A61K 35/50* (2013.01); *C12N 5/0605* (2013.01); *C12N 5/0667* (2013.01); *A61K 35/12* (2013.01)

(58) Field of Classification Search
None
See application file for complete search history.

(56) References Cited

U.S. PATENT DOCUMENTS

| | | | |
|---|---|---|---|
| 5,516,532 A | 5/1996 | Atala et al. | |
| 5,654,381 A | 8/1997 | Hrkach et al. | |
| 5,709,854 A | 1/1998 | Griffith-Cima et al. | |
| 7,078,230 B2 | 7/2006 | Wilkison et al. | |
| 2002/0155096 A1* | 10/2002 | Chancellor et al. | 424/93.7 |
| 2003/0032179 A1 | 2/2003 | Hariri | |
| 2003/0235563 A1 | 12/2003 | Strom et al. | |
| 2005/0255592 A1 | 11/2005 | Collins et al. | |
| 2008/0241113 A1 | 10/2008 | Walton et al. | |
| 2010/0266553 A1 | 10/2010 | Ra et al. | |

FOREIGN PATENT DOCUMENTS

| | | |
|---|---|---|
| KR | 10-2006-0057738 A | 5/2006 |
| KR | 10-2006-0067199 A | 6/2006 |
| KR | 10-0679642 B1 | 1/2007 |
| KR | 10-2007-0101756 A | 10/2007 |
| KR | 10-0773460 B1 | 10/2007 |
| KR | 10-2007-0119497 A | 12/2007 |
| KR | 10-2008-0097593 A | 11/2008 |
| KR | 10-2008-0103637 A | 11/2008 |
| WO | WO 96/39101 A1 | 12/1996 |

OTHER PUBLICATIONS

Palma PCR et al. 1997. Repeated lipoinjections for stress urinary incontinence. J Endourol 11: 67-70.*
Cousin et al., "Reconstitution of lethally irradiated mice by cells isolated from adipose tissue", Biochemical and Biophysical Research Communications, 301:1016-1022 (2003).
Fukuoka et al., "Cloning and characterization of the guinea pig C5a anaphylatoxin receptor: interspecies diversity among the C5a receptors", International Immunology, vol. 10, No. 3, pp. 275-283 (1998).
Gronthos et al., "Surface Protein Characterization of Human Adipose Tissue-Derived Stromal Cells", Journal of Cellular Physiology, vol. 189:54-63 (2001).
Jiang, Y. et al., "Multipotent progenitor cells can be isolated from postnatal murine bone marrow, muscle, and brain", Experimental Hematology, 30:896-904 (2002).
Jiang et al., "Pluripotency of mesenchymal stem cells derived from adult marrow", Nature, vol. 418, pp. 41-49 (2002).
Lin et al., "Accelerated Growth and Prolonged Lifespan of Adipose Tissue-derived Human Mesenchymal Stem cells in a Medium Using Reduced Calcium and Antioxidants", Stem Cells and Development, vol. 14:92-102 (2005).
Miranville et al., "Improvement of Postnatal Neovascularization by Human Adipose Tissue-Derived Stem Cells", Circulation, 110:349-355 (2004).
Rodriguez et al., "Adipocyte differentiation of multipotent cells established from human adipose tissue", Biochemical and Biophysical Research Communications, 315:225-263 (2004).
Sampaolesi et al., Cell Therapy of μ-Sarcoglycan Null Dystrophic Mice Through Intra-Arterial Delivery of Mesoangioblasts, Science, vol. 301, pp. 487-492 (Jul. 25, 2003).
Seo et al., "Differentiation of human adipose stromal cells into hepatic lineage in vitro and in vivo", Biochemical and Biophysical Research Communications, 328:258-264 (2005).
Simmons et al., "Isolation of a cDNA Encoding CD33, a Differentiation Antigen of Myeloid Progenitor Cells", The Journal of Immunology, vol. 141, 2797-2800, No. 8 (Oct. 15, 1998).

(Continued)

*Primary Examiner* — Lora E Barnhart Driscoll
(74) *Attorney, Agent, or Firm* — Rabin & Berdo, P.C.

(57) ABSTRACT

The present invention relates to a cellular therapeutic agent for treating urinary incontinence, and more particularly to a cellular therapeutic agent for treating urinary incontinence, which contains stem cells derived from the decidua of the placenta or menstrual fluid or stem cells derived from adipose. The decidua-derived stem cells or adipose-derived stem cells show the effects of increasing leak point pressure and urethral sphincter contractility, and thus are useful as an agent for treating urinary incontinence.

1 Claim, 20 Drawing Sheets

(56) References Cited

OTHER PUBLICATIONS

Tomas et al., "Isolation of multipotent adult stem cells from the dermis of mammalian skin", Nature Cell Biology, vol. 3, pp. 778-784 (Sep. 2001).

Verfaillie, C., "Adult stem cells: assessing the case for pluripotency", Trends in Cell Biology, vol. 12, No. 11 (Nov. 2002).

Zuk et al., "Multilineage Cells from Human Adipose Tissue: Implications for Cell-Based Therapies", Tissue Engineering, vol. 7, No. 2 (2001).

Feki, A. et al., "Sphincter incontinence: Is regenerative medicine the best alternative to restore urinary or anal sphincter function?", The Intl Jrl. Of Biochem. & Cell Bio., 39: 678-684 (2007).

Furuta, A. et al., "The potential of muscle-derived stem cells for stress urinary incontinence", Expert Opin. Biol. Ther. 7(10): 1483-1486 (2007).

* cited by examiner

Decidua-MSC p2 Myogenesis
Control

DAPI (Nuclear staining)      FITC

αMyosin

DAPI

FITC      Merge

CELLULAR THERAPEUTIC AGENT FOR INCONTINENCE OR URINE COMPRISING STEM CELLS ORIGINATED FROM DECIDUA OR ADIPOSE

CROSS-REFERENCE TO RELATED APPLICATION

This application claims priority from Korean Patent Application No. 10-2007-0124010 filed on Nov. 30, 2007 in the Korean Intellectual Property Office. This application is also continuation of application Ser. No. 12/668,592 filed on Nov. 20, 2010, the disclosure of which is incorporated herein by reference in its entirety.

TECHNICAL FIELD

The present invention relates to a cellular therapeutic agent for treating urinary incontinence, and more particularly to a cellular therapeutic agent for treating urinary incontinence, which contains stem cells derived from the decidua of the placenta or menstrual fluid or stem cells derived from adipose tissue.

BACKGROUND ART

Stem cells refer to cells having not only self-replication ability but also the ability but also the ability to differentiate into at least two cells, and can be divided into totipotent stem cells, pluripotent stem cells, and multipotent stem cells.

Totipotent stem cells are cells with totipotent properties capable of developing into one perfect individual, and these properties are possessed by cells up to the 8-cell stage after the fertilization of an oocyte and a sperm. When these cells are isolated and transplanted into the uterus, they can develop into one perfect individual. Pluripotent stem cells, which are cells capable of developing into various cells and tissues derived from the ectodermal, mesodermal and endodermal layers, are derived from an inner cell mass located inside blastocysts generated 4-5 days after fertilization. These cells are called "embryonic stem cells" and can differentiate into various other tissue cells but not form new living organisms. Multipotent stem cells are stem cells capable of differentiating into only cells specific to tissues and organs containing these cells.

The multipotent stem cells were first isolated from adult bone marrow (Y. Jiang et al., *Nature*, 418:41, 2002), and then also found in other various adult tissues (C. M. Verfaillie, *Trends Cell Biol.*, 12:502, 2002). In other words, although bone marrow is the most widely known source of stem cells, the multipotent stem cells were also found in the skin, blood vessels, muscles and brains (J. G. Tomas et al., *Nat. Cell Biol.*, 3:778, 2001; M. Sampaolesi et al., *Science*, 301:487, 2003; Y. Jiang et al., *Exp. Hematol.*, 30:896, 2002). However, stem cells are very rarely present in adult tissues, such as bone marrow, and such cells are difficult to culture without inducing differentiation, and thus difficult to culture in the absence of specifically screened media. Namely, it is very difficult to maintain the isolated stem cells in vitro.

Recently, adipose tissue was found to be a new source of multipotent stem cells (B. Cousin et al., *BBRC.*, 301:1016, 2003; A. Miranville et al., *Circulation*, 110:349, 2004; S. Gronthos et al., *J. Cell Physiol.*, 189:54, 2001; M. J. Seo et al., *BBRC.*, 328:258, 2005). Namely, it was reported that a group of undifferentiated cells is included in human adipose tissue obtained by liposuction and has the ability to differentiate into fat cells, osteogenic cells, myoblasts and chondroblasts (P. A. Zuk et al., *Tissue Eng.*, 7:211, 2001; A. M. Rodriguez et al., *BBRC.*, 315:255, 2004). This adipose tissue has an advantage in that it can be extracted in large amounts, and thus, it receives attention as a new source of stem cells, which can overcome the existing shortcomings. Also, recent studies using animal model experiments disclose that adipose tissue-derived cells have the abilities to regenerate muscles and stimulate the differentiation of neural blood vessels. Thus, these adipose tissue-derived cells are being attention as a new source of stem cells.

The present inventors have previously cultured finely cut placenta tissue in a medium containing collagenase and bFGF, isolated placenta stem cells from the culture broth, and then allowed the isolated stem cells to differentiate into myocytes, osteogenic cells, neurocytes, adipocytes, chondrocytes and pancreatic beta cells (Korean Patent Publication No. 2007-0101756 A).

Meanwhile, urinary incontinence in women is caused by sagging of the urethra and bladder, which results from weakening of pelvic floor muscles arising from pudendal nerve injury due to frequent childbirth and aging. Currently, the number of female urinary incontinence patients in Korea is estimated to be about 4,000,000-5,000,000 and is increasing every year due to a rapid increase in the number of old age women. Thus, female urinary incontinence is becoming one of serious social problem worldwide. To treat urinary incontinence patients, injection therapy or surgical therapy for supporting the urethra and bladder are used. Currently, the surgical therapy which is an invasive method has a problem in that complications can occur, and the injection therapy has problems in that it employs expensive substances, and thus cannot be easily applied to all patients, and in that it has a success rate of only 50-60%, such that injection and surgery are required again.

Stem cell injection therapy does not need anesthesia and enables easy injection of stem cells into urethral sphincter. Thus, if the stem cell injection therapy can improve the contractility of urethral sphincter and increase leak point pressure, the stem cell therapy can be advantageously used to treat urinary incontinence. However, there is no study on the use of stem cells for treating urinary incontinence.

Accordingly, the present inventors have made many efforts to develop an agent for treating urinary incontinence containing stem cells and, as a result, found that placental decidua-derived stem cells or adipose-derived stem cells are effective for the treatment of urinary incontinence, thereby completing the present invention.

SUMMARY OF INVENTION

It is therefore a main object of the present invention to provide cellular therapeutic agent for treating urinary incontinence, which contains, as an active ingredient, stem cells derived from the decidua of the placenta or menstrual fluid or stem cells derived from adipose.

Another object of the present invention is to provide a method for preparing cellular therapeutic agent for treating urinary incontinence, which contains, as an active ingredient, stem cells derived from the decidua of the placenta or menstrual fluid or stem cells derived from adipose.

Still another object of the present invention is to provide the use of stem cells derived from the decidua of the placenta or menstrual fluid or stem cells derived from adipose for preventing or treating urinary incontinence.

Other features and embodiments of the present invention will be more apparent from the following detailed description and the appended claims.

DETAILED DESCRIPTION OF THE INVENTION AND PREFERRED EMBODIMENTS

Figure 1:
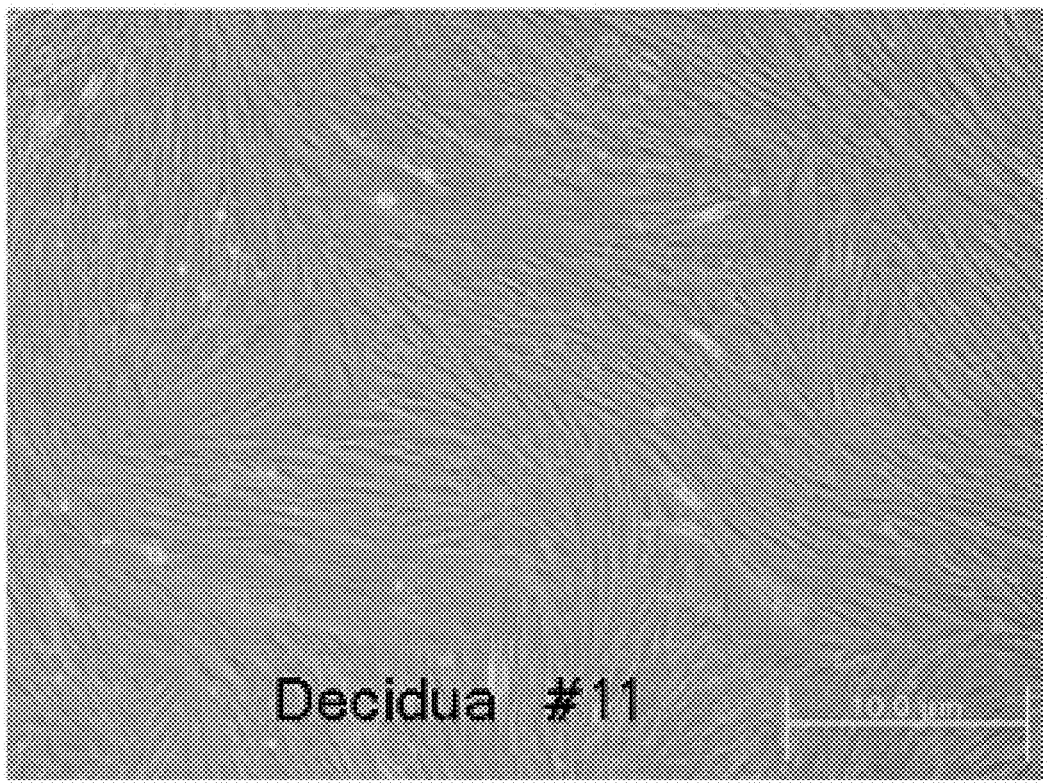
FIG. 1 is a microscopic photograph showing the morphology of mesenchymal stem cells (MSCs) derived from the decidua of the placenta.

In one aspect, the present invention relates to a cellular therapeutic agent for treating urinary incontinence, which contains stem cells derived from the decidua of the placenta or menstrual fluid or stem cells derived from adipose, as an active ingredient.

In the present invention, the stem cells derived from the decidua of the placenta have the following characteristics: (a) showing immunophenotypes positive for CD29 and CD90, but negative for CD31 and CD45; (b) showing immunophenotypes positive for Oct4, SSEA-4 and Cripto-1; (c) growing attached to plastic, showing morphological features of round or spindle shape, and forming spheres in SFM medium so as to be able to be maintained in an undifferentiated state for a long period of time; and (d) having the ability to differentiate into myocytes.

1. Definition of Terms

As used herein, the term "stem cell" refers to a master cell that can reproduce indefinitely to form the specialized cells of tissues and organs and includes developmentally pluripotent and multipotent stem cells. A stem cell can divide to produce two daughter stem cells, or one daughter stem cell and one progenitor ("transit") cell, which then proliferates into the tissue's mature, fully formed cells.

As used herein, the term "differentiation" refers to a phenomenon in which the structure or function of cells is specialized during the division, proliferation and growth thereof, that is, the feature or function of cell or tissue of an organism changes in order to perform work given to the cell or tissue. Generally, it refers to a phenomenon in which a relatively simple system is divided into two or more qualitatively different partial systems. For example, it means that a qualitative difference between the parts of any biological system, which have been identical to each other at the first, occurs, for example, a distinction, such as a head or a body, between egg parts, which have been qualitatively identical to each other at the first in ontogenic development, occurs, or a distinction, such as a muscle cell or a nerve cell, between cells, occurs, or the biological system is divided into qualitatively distinguishable parts or partial systems as a result thereof.

As used herein, the term "cellular therapeutic agent" refers to a drug used for the purpose of treatment, diagnosis and prevention, which contains a cell or tissue prepared through isolation from humans, culture and specific operation (as provided by the US FDA). Specifically, it refers to a drug used for the purpose of treatment, diagnosis and prevention through a series of behaviors of in vitro multiplying and sorting living autologous, allogenic and xenogenic cells or changing the biological characteristics of cells by other means for the purpose of recovering the functions of cells and tissues. Cellular therapeutic agents are broadly divided, according to the differentiation level of cells, into somatic cell therapeutic agents and stem cell therapeutic agents. The present invention particularly relates to a cellular therapeutic agent containing decidua-derived stem cells or adipose-derived stem cells.

2. Isolation and Purification of Decidua-Derived Stem Cells

The placenta is formed for an embryo during pregnancy and is generally in the shape of a disk having a weight of about 500 g, a diameter of about 15-20 cm and a thickness of 2-3 cm. One side of the placenta is in contact with the mother body, and the other side is in contact with an embryo. The space in the placenta contains the mother's blood for supplying nutrients to an embryo. The placenta consists of three layers: amnion, chorion and decidua. The amnion is a thin clear membrane surrounding an embryo and contains amniotic fluid, and the stem cells of an embryo are present in the amnion. The decidua is a membrane formed as a result of a process in which the epithelial cells of the uterus are modified so that a fertilized egg becomes implanted in the uterine wall. The decidua contains mother's stem cells. In the present invention, stem cells were isolated from the decidua.

Decidua-derived stem cells isolated from the human term placenta according to the present invention are classified as autologous adult stem cells, which do not cause ethical problems, because they are derived from placenta tissue.

Stem cells are generally isolated and purified from the placental decidua through the following method. After expulsion of mammalian placenta (preferably human placenta) from the uterus, the decidua is isolated from the placenta, treated and cultured to produce multipotent stem cells, placental decidua-derived stem cells and other biomaterials. Placental decidua-derived stem cells are obtained from the placenta expulsed from the uterus. In a preferred embodiment, the placenta is cultured in the presence of growth factors, for example, bFGF (Basic Fibroblast Growth Factor).

In the present invention, stem cells were isolated and purified from human placental decidua through the following method. Decidua tissues were isolated from human placental tissue samples and washed with PBS, and then the decidua tissues are finely cut. The finely cut decidua tissues were transferred into a 100-mm dish, and then chemically degraded in collagenase (1 mg/ml)-containing DMEM (Dulbecco's Modified Eagle Medium, Gibco) at 37° C. for 1 hour.

The chemically decomposed tissues were filtered through a 100-μm mesh to remove non-decomposed tissues, and then centrifuged at 1200 rpm for 1-10 minutes. The supernatant was suctioned, and pellets remaining on the bottom were washed with PBS, and then centrifuged at 1200 rpm for 1-10 minutes. The pellets remaining on the bottom were well suspended as single cells, and then cultured in a bFGF-containing DMEM medium. At this time, mesenchymal stem cells were attached to the bottom, and the other cells were suspended.

Such placental decidua-derived stem cells grew attached to plastic and showed morphological features of round and spindle shape. After two days, cells unattached to the dish bottom were washed with PBS and cultured while replacing the medium at an interval of 2-3 days, thus obtaining a solution of decidua-derived stem cells isolated from the human placenta.

Figure 2:
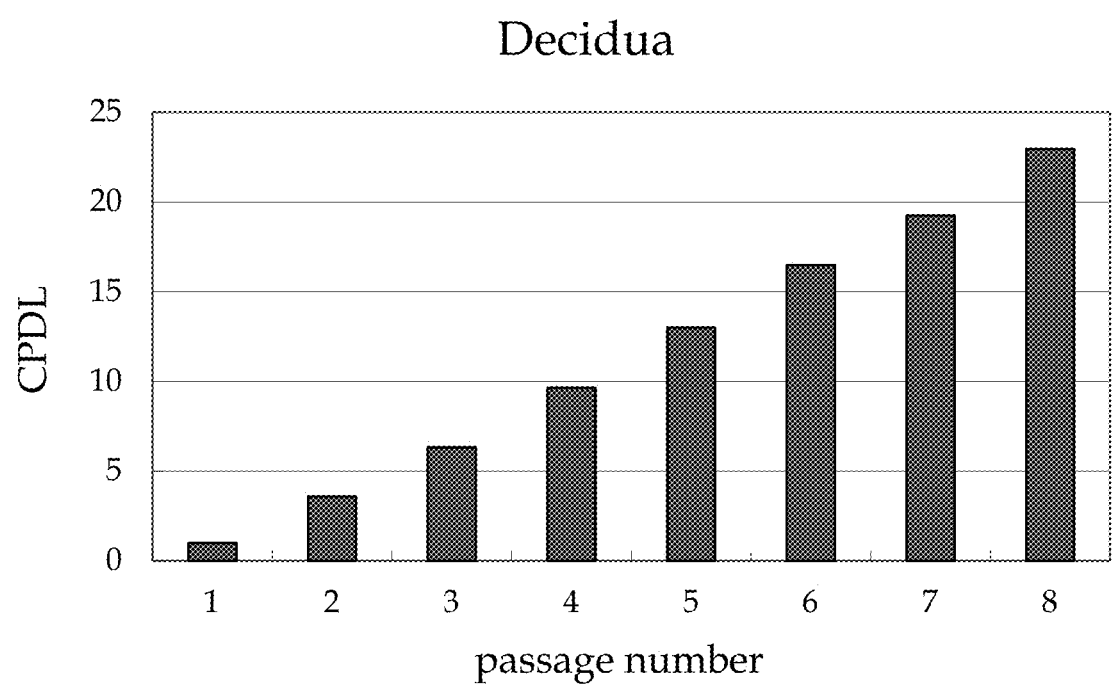
FIG. 2 is a graphic diagram showing the cumulative population doubling level (CPDL) as a function of passage number of decidua-derived stem cells.

The proliferation rate of the isolated decidua-derived stem cells was examined and, as a result, it could be seen that these cells showed a gradual increase in CPDL up to passage number 12, suggesting that these cells had high proliferation rate (FIG. 2).

Figure 3:
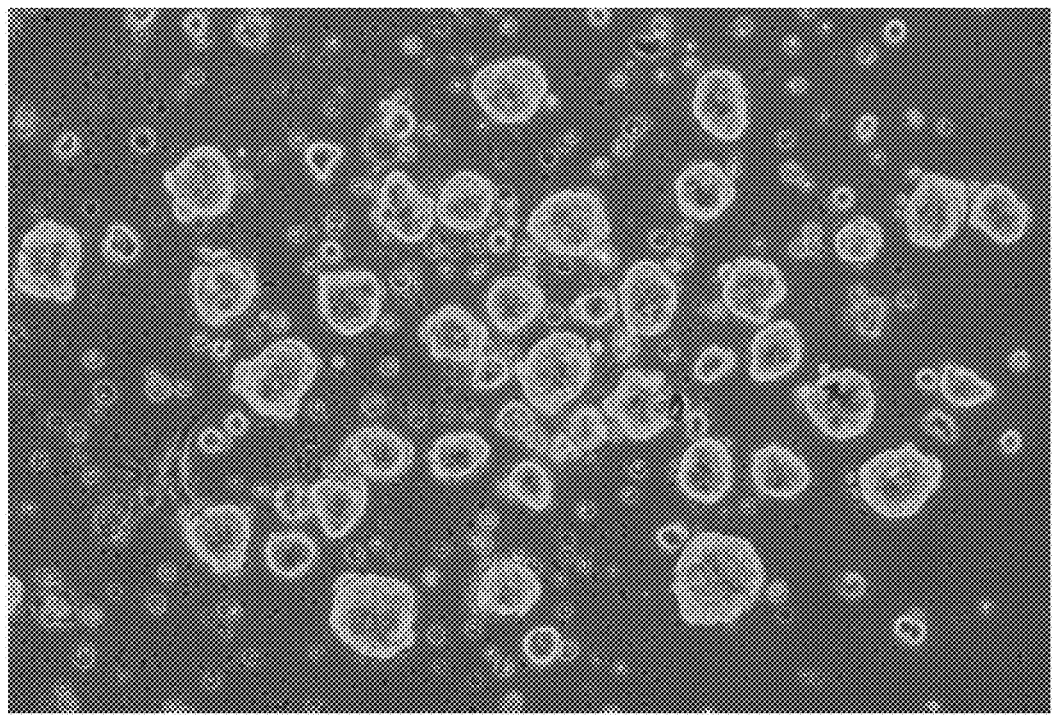
FIG. 3 is a photograph showing that the first-passage decidual cells cultured in SFM medium formed spheres.

The obtained stem cells derived from the placental decidua form spheres in SFM medium, and thus can be maintained in an undifferentiated state for a long period of time (FIG. 3). One example of SFM medium usable in the present invention may be MEBM (mammary epithelial basal medium) containing 2% B27, 500 mM 2-mercaptoethanol, 1 μg/ml hydrocortisone, 5 μg/ml insulin, 20 ng/ml EGF and 20 ng/ml bFGF.

The number and type of proliferated cells can easily be monitored by measuring changes in morphology and cell surface markers using standard cell detection techniques such as flow cytometry, cell sorting, immunocytochemistry (e.g., staining with tissue specific or cell-marker specific antibodies), fluorescence activated cell sorting (FACS), magnetic activated cell sorting (MACS), or by examining the morphology of cells using an optical microscope or confocal microscope, or by measuring changes in gene expression using techniques well known in the art, such as PCR and gene expression profiling.

In a preferred embodiment, stem cells derived from the decidua of the placenta or menstrual fluid are sorted using techniques known in the art, for example, density gradient centrifugation, magnetic cell separation, flow cytometry and other cell separation methods.

Methods of obtaining multipotent stem cells expressing the desired surface antigens from stem cell broth derived from decidua of the placenta or menstrual fluid obtained above include a FACS method using a flow cytometer with sorting function (*Int. Immunol.*, 10(3):275, 1998), a method using magnetic beads, and a panning method using an antibody specifically recognizing multipotent stem cells (*J. Immunol.*, 141(8):2797, 1998). Also, methods for obtaining multipotent stem cells from a large amount of culture broth include a method where antibodies specifically recognizing molecules expressed on the surface of cells (hereinafter, referred to as "surface antigens") are used alone or in combination as columns.

Flow cytometry sorting methods may include a water drop charge method and a cell capture method. In one embodiment, cell surface marker-specific antibodies or ligands are labeled with distinct fluorescent labels. Cells are processed through a cell sorter, allowing separation of cells based on their ability to bind to the antibodies used. FACS-sorted particles may be directly deposited into individual wells of 96-well or 384-well plates to facilitate separation and cloning.

In any of these methods, an antibody specifically recognizing an antigen on the cell surface is fluorescently labeled, the intensity of fluorescence emitted from an antibody bonded with the molecule expressed on the surface of the cell is converted to an electric signal whereby the expressed amount of the antigen can be quantified. It is also possible to separate cells expressing a plurality of surface antigens by combination of fluorescence types used therefor. Examples of fluorescences which can be used in this case include FITC (fluorescein isothiocyanate), PE (phycoerythrin), APC (allophycocyanin), TR (Texas Red), Cy 3, CyChrome, Red 613, Red 670, TM-Color, Quantum Red, etc.

FACS methods using a flow cytometer include: a method where the above stem cell broth is collected, from which cells are isolated by, for example, centrifugation, and stained directly with antibodies; and a method where the cells are cultured and grown in a suitable medium and then stained with antibodies. The staining of cells is performed by mixing a primary antibody recognizing a surface antigen with a target cell sample and incubating the mixture at 4° C. for 30 minutes to 1 hour. When the primary antibody is fluorescently labeled, the cells are isolated with a flow cytometer after washing. When the primary antibody is not fluorescently labeled, cells reacted with the primary antibody and a fluorescent labeled secondary antibody having binding activity to the primary antibody are mixed after washing, and incubated at 4° C. for 30 minutes to 1 hour. After washing, the cells stained with the primary and secondary antibodies are isolated with a flow cytometer.

The above-described method for isolating and purifying the decidua-derived stem cells can also be easily applied to the adipose-derived stem cells of the present invention.

3. Characteristics of Stem Cells Derived from Placental Decidua

The stem cells isolated from the placental decidua are homogenous and sterile. Furthermore, the stem cells are readily obtained in a form suitable for administration to humans, that is, they are of pharmaceutical grade.

After long-term culture, cells can be characterized with CD-series of surface antigen markers, for example, CD29 (mononuclear cell marker), CD31 (endothelial cell and stem cell marker), CD45 (hematopoietic cell marker) and CD90 (mononuclear stem cell marker), and can be applied to FACS analysis.

Preferred placental decidua-derived stem cells obtained by the method of the present invention may be identified by the presence of cell surface markers having the following characteristics: showing immunophenotypes positive for CD29 and CD90, but negative for CD31 and CD45. Such cell surface markers are routinely determined according to methods well known in the art, e.g. by flow cytometry, followed by washing and staining with an anti-cell surface marker antibody.

Figure 4:
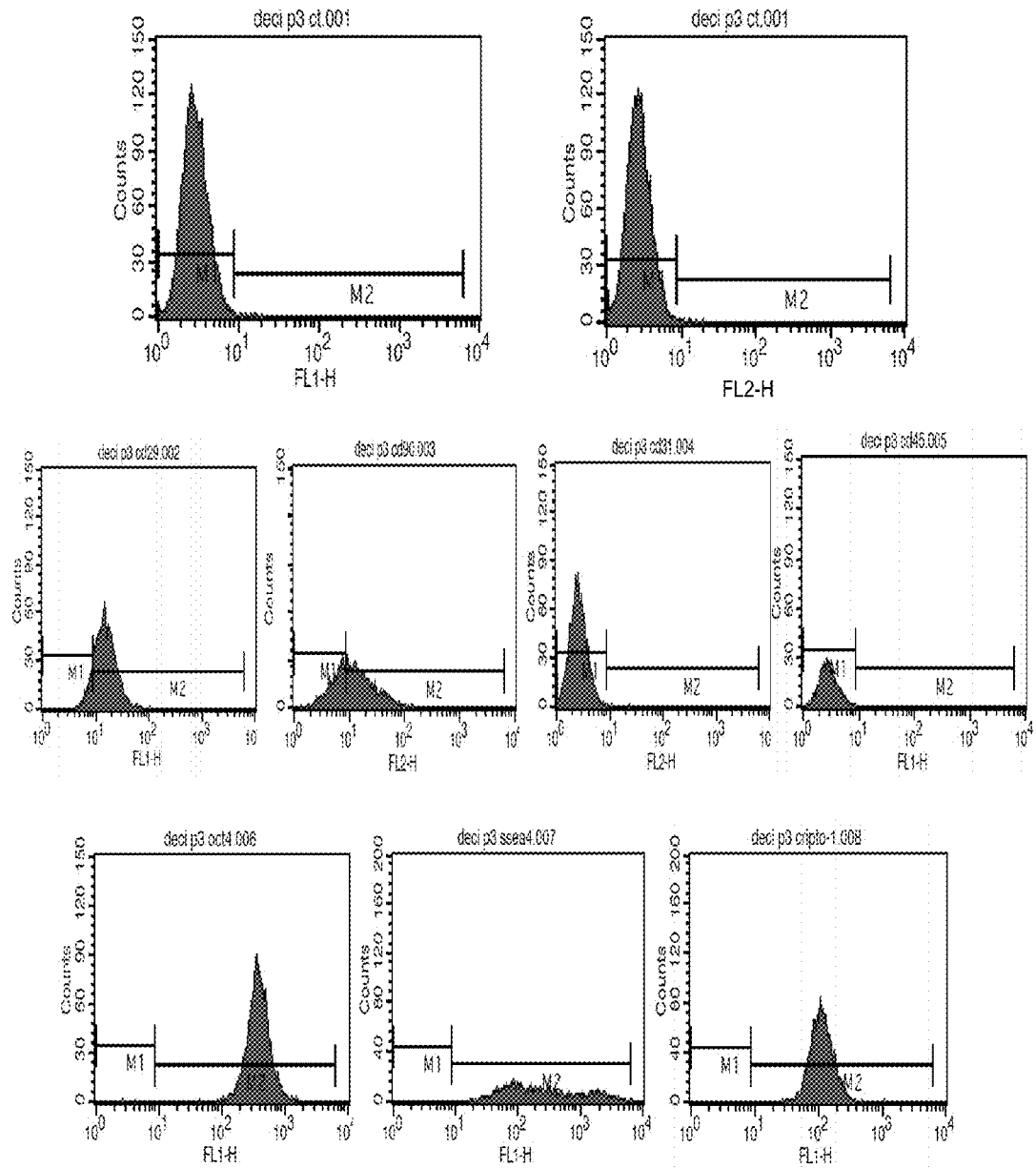
FIG. 4 is a photograph showing the results obtained by analyzing the surface antigens of decidua-derived MSCs using a flow cytometer (FACS).
Figure 5:
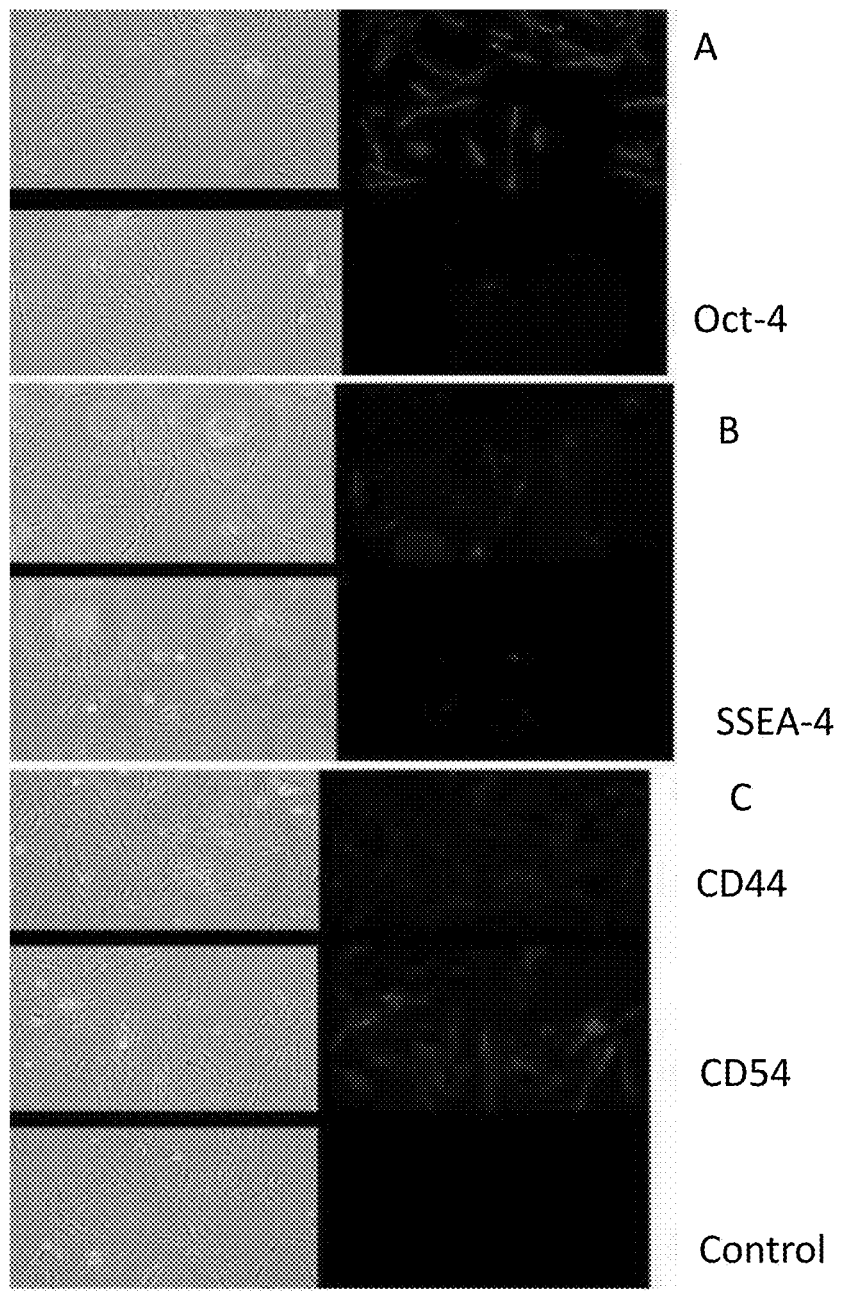
FIG. 5 is a photograph showing the results of immunocytochemical analysis performed using the indicated antibodies [A: OCT4; B: SSEA4; and C: CD44, CD54 and control].
Figure 6:
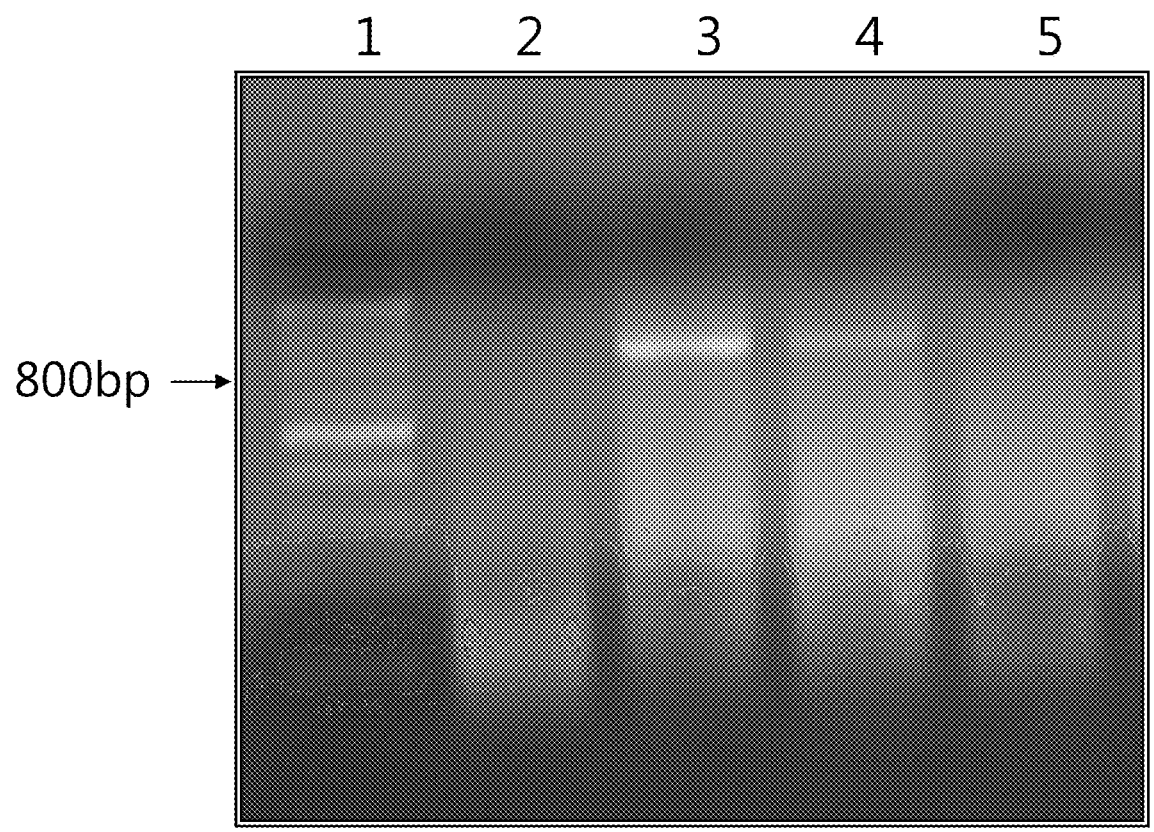
FIG. 6 shows the results of RT-PCR for OCT4 [lane 1: marker; lane 2: RT-reaction control; lane 3: amniotic stem cells; lane 4: decidua-derived stem cells; and lane 5: PCR-reaction control].

Also, the placental decidua-derived stem cells according to the present invention can be identified using Oct4, SSEA4 and Cripto-1 markers that can be considered as an undifferentiated marker for stem cells (FIGS. 4, 5 and 6). Oct4 is well known as an undifferentiated marker for stem cells, and it is general to test Oct4 expression ability in order to identify stem cells in an undifferentiated state, as disclosed in Korean Patent Application No. 10-2004-0105716, entitled "Monoclonal antibody specific to human embryonic stem cells", Korean Patent Application No. 10-2004-0096780, entitled "Double-stranded RNA for inhibition of expression of Oct4 gene that maintains undifferentiated state of mammalian embryonic stem cells", Korean Patent Application No. 10-2006-0092128, entitled "Human umbilical cord blood-derived multipotent stem cells having increased ability to proliferate due to osteoblast-based structure and preparation method thereof", and the like. Also, it is well known that SSEA4 (stage specific embryonic antigen 4) and Cripto-1 are present on the surface of human embryonic stem cells.

The expression of Oct4 is confirmed using RT-PCR (Reverse Transcriptase-Polymerase Chain Reaction) together with FACS. The method of RT-PCR is a technique known in the art. RT-PCR is a technique comprising synthesizing corresponding cDNA using RNA of a specific region as a template and carrying out PCR amplification using the cDNA, and consists of the steps of (1) preparing cDNA from RNA using reverse transcriptase, and (2) amplifying a specific region using the cDNA, and the step (2) is the same as a method of amplifying a specific gene region from genomic DNA. This method can be performed in a simple manner compared to RNA analysis which has been possible through methods such as Northern blot hybridization, and it allows the base sequence of a gene to be determined. Thus, this method is greatly useful mainly in studying the base sequence and transcription level of mRNA.

The placental decidua-derived stem cells of the present invention are positive for the expression of Oct4, SSEA4 and Cripto-1 (FIGS. 4, 5 and 6).

4. Differentiation of Placental Deciduas-Derived Stem Cells

The placental decidua-derived stem cells obtained according to the inventive method can be induced to differentiate along specific cell lineages, including differentiation into myocytes. In a specific embodiment, the placental decidua-derived stem cells obtained according to the inventive method are induced to differentiate for use in transplantation and ex vivo treatment protocols. In a specific embodiment, the placental decidua-derived stem cells obtained according to the inventive method are induced to differentiate into a particular cell type and are genetically engineered to provide a therapeutic gene product.

The differentiation of the placental decidua-derived stem cells into particular myocytes can be measured according to any method known in the art, and the placental decidua-derived stem cells can be induced to differentiate into myocytes by pretreating the placental decidua-stem cells with azacytidine for one day and then culturing the pretreated cells in SKBM medium (Cambrex, Co.).

Determination that the stem cells have differentiated into myocytes can be accomplished by methods well-known in the art, e.g., measuring changes in morphology and cell surface markers (e.g., staining cells with tissue-specific or cell-marker specific antibodies) using techniques such as flow cytometry or immunocytochemistry, or by examining the morphology of cells using an optical microscope or confocal microscope, or by measuring changes in gene expression using techniques well known in the art, such as PCR and gene-expression profiling.

5. Use of Placental Deciduas-Derived Stein Cells and Cells Differentiated Therefrom The placental decidua-derived stem cells according to the present invention can be used for a wide variety of therapeutic protocols in which the tissue or organ of the body is augmented, repaired or replaced by the engraftment, transplantation or infusion of a desired cell population, such as a placental decidua-derived stem cell or placental decidua-derived stem cell population. The placental decidua-derived stem cells of the present invention can be used to replace or augment existing tissues to grow new or altered tissues, or to bond the tissues with biological tissues or structures.

In a preferred embodiment of the present invention, the placental decidua-derived stem cells may be used in autologous and allogenic transplants, including HLA-matched and HLA-mismatched hematopoietic transplantations.

The placental decidua-derived stem cells of the present invention may be used instead of specific classes of progenitor cells (e.g., chondrocytes, stem cells, hematopoietic cells, pancreatic parenchymal cells, neuroblasts, muscle progenitor cells, etc.) in therapeutic or research protocols in which progenitor cells would typically be used.

In addition, the placental decidua-derived stem cells of the present invention may be formulated as injectable preparations (e.g., WO 96/39101 incorporated herein by reference in its entirety). In an alternative embodiment, the cells and tissues of the present invention may be formulated using polymerizable or cross-linking hydrogels as described in U.S. Pat. Nos. 5,709,854, 5,516,532 and 5,654,381, each of which is incorporated herein by reference in their entirety.

6. Adipose-Derived Stem Cells and Use Thereof

The adipose-derived stem cells of the present invention are obtained from adipose tissue harvested through liposuction, and grow attached to a plastic culture dish.

Specifically, the adipose-derived stem cells of the present invention are adipose-derived stem cells, isolated and cultured according to the disclosure of Korean Patent Application No. 10-2007-0050624, Korean Patent Application No. 10-2007-0042645, Korean Patent Registration No. 10-0679642 or Korean Patent Registration No. 10-0788632, which were filed by the applicant.

The adipose-derived adult stem cells have the following characteristics:

(a) showing positive immunological responses to all of CD73, CD90, CD29, CD44 and CD105, and negative immunological responses to all of CD133, CD34, CD45, CD4, CD31, CD62p, CD14 and HLA-DR; and (b) growing attached to a plastic material, showing morphological feature of spindle shape, and forming spheres in a medium containing CORM-2 so as to be able to be maintained in an undifferentiated state for a long period of time.

In the present invention, for the sphere culture of the stem cells of the present invention, the isolated adipose-derived multipotent stem cells were cultured in a CORM-2-containing MEBM and, as a result, they started to form spheres from 3 days after seeding. This suggests that the adipose-derived stem cells are maintained in an undifferentiated state, and thus have high proliferation rates.

Also, in order to examine the immunological properties of the adipose-derived stem cells, according to, but not limited to, the analysis of immunological characteristics described in the above-mentioned patent documents, the adipose-derived stem cells were washed with PBS and treated with trypsin. The treated cells were collected and centrifuged at 1000 rpm for 5 minutes. After the supernatant was discarded, the cells were washed with a mixture of 2% FBS and PBS, followed by centrifugation at 1000 rpm for 5 minutes. After this, the supernatant was discarded, and then the cells were suspended in PBS and dispensed into a well plate at a density of $1\times10^5$ cells for each sample. An antibody (R-phycoerythrin-conjugated mouse anti-human monoclonal antibody) was placed into each well and incubated on ice for 40 minutes to induce the binding thereof. After the incubation, the cell suspension was centrifuged at 1000 rpm for 5 minutes, the supernatant was removed, and the cells were washed twice with PBS. Then, the cells were fixed with 1% paraformaldehyde, and the surface antigens of the obtained multipotent stem cells were analyzed by FACS. As a result, the inventive adipose-derived multipotent stem cells were positive for CD73 (91%), CD90 (97%), CD29 (96%), CD44 (83%) and CD105 (80%). Also, the immunophenotypes of the multipotent stem cells for other antigens were analyzed and, as a result, the cells were negative for CD133, CD34, CD45, CD4, CD31, CD62p, CD14 and HLA-DR.

The adipose-derived multipotent stem cells were stored in each of saline, saline+sucrose, saline+sucrose+5% albumin, and PBS+sucrose, and then analyzed for the ability to form spheres. For this purpose, the adipose-derived multipotent stem cells were seeded and cultured in each well of a 6-well culture plate containing a serum-free MEBM medium (containing 10 μg/ml CORM-2, 5 ml antibiotic-antimycotic solution (100×), 1 μg/ml hydrocortisone, 5 μg/ml insulin, 20 ng/ml EGF, 40 ng/ml FGF, B27 and β-mercaptoethanol) at a cell concentration of $5\times10^4$-$1\times10^5$ cells/ml. As a result, the stem cells started to form spheres from 3-7 days after the seeding, and the stem cells proliferated to form spheres even at 7-10 days after the seeding.

In one embodiment of the present invention, adipose-derived stem cells are obtained by preparing raw materials containing tumescent solution and fatty tissue obtained from liposuction or a disposable syringe having a catheter connected thereto, subjecting the raw materials to a mycoplasma test and a sterility test, selecting a sample satisfying the quality standards, from among the raw materials, centrifuging the selected sample into a fatty layer and an aqueous layer, pretreating the sample of the aqueous layer with a collagenase solution, and then culturing the resulting cells in the medium disclosed in the above-mentioned patent documents.

The adipose-derived stem cells according to the present invention can be used for a wide variety of therapeutic protocols in which the tissue or organ of the body is augmented, repaired or replaced by the engraftment, transplantation or infusion of a desired cell population, such as an adipose-derived stem cell or adipose-derived stem cell population. The adipose-derived stem cells of the present invention can be used to replace or augment existing tissues to grow new or altered tissues, or to bond the tissues with biological tissues or structures.

The adipose-derived stem cells obtained according to the inventive method can be induced to differentiate along specific cell lineages, including differentiation into myocytes. In a specific embodiment, the adipose-derived stem cells obtained according to the inventive method are induced to differentiate for use in transplantation and ex vivo treatment protocols. In a specific embodiment, the adipose-derived stem cells obtained according to the inventive method are induced to differentiate into a particular cell type and are genetically engineered to provide a therapeutic gene product. The differentiation of the adipose-derived stem cells into particular myocytes can be measured according to any method known in the art.

Determination that the stem cells have differentiated into myocytes can be accomplished by methods well-known in the art, e.g., measuring changes in morphology and cell surface markers (e.g., staining cells with tissue-specific or cell-marker specific antibodies) using techniques such as flow cytometry or immunocytochemistry, or by examining the morphology of cells using an optical microscope or confocal microscope, or by measuring changes in gene expression using techniques well known in the art, such as PCR and gene-expression profiling.

7. Development of Agent for Treating Urinary Incontinence Containing Stem Cells Derived from Placental Decidua or Adipose The inventive cellular therapeutic agent for treating urinary incontinence containing placental decidua-derived or adipose-derived stem cells is based on the principle in which the placental decidua-derived stem cells or adipose-derived stem cells increase leak point pressure, indicating an improvement in the function of internal urethral sphincter, and increase urethral sphincter contractility, indicating an improvement in the function of external urethral sphincter.

As used herein, the term "leak point pressure" refers to either the intravesical pressure at the time of leakage of urine or Valsalva leak point pressure, and the decrease in leak point pressure is a major cause of urinary incontinence.

In the present invention, in order to measure the effect of the placental decidua-derived stem cells or adipose-derived stem cells on the treatment of urinary incontinence, particularly on leak point pressure, female nude mice were divided into a normal group, a control group and experimental groups. Then, the intravesical pressure in each of the normal group, the control group (in which the pudendal nerve was cut) and the experimental groups (in which the pudendal nerve was cut, and then injected with the placental decidua-derived stem cells or adipose-derived stem cells) was increased, and leak point pressure in each group was measured. As a result, it was confirmed that the placental decidua-derived stem cells according to the present invention increase leak point pressure, and thus can be used as an agent for treating urinary incontinence.

The urethral sphincter muscle functions to regulate urination due to the contractility thereof, and weakening of the urethral sphincter muscle is also a major cause of urinary incontinence.

In the present invention, in order to measure the effect of the placental decidua-derived stem cells or adipose-derived stem cells on the treatment of urinary incontinence, particularly on urethral sphincter contractility, male mice were divided into a normal group, a control group and experimental groups. Then, the urethral tissue segment of each group was applied with electrical field stimulation or an acetylcholine drug, and urethral sphincter contractility in each group was measured. As a result, it was confirmed that the placental decidua-derived stem cells or adipose-derived stem cells according to the present invention increased urethral sphincter contractility, and thus can be used as a cellular therapeutic agent for treating urinary incontinence.

8. Cellular Therapeutic Agent for Treating Urinary Incontinence Containing Stem Cells Derived from Placental Decidua, Stem Cells Derived from Decidua of Menstrual Fluid or Stem Cells Derived from Adipose As used herein, the term "placental decidua refers to a membrane formed as a result of a process in which the epithelial cells of the uterus are modified so that a fertilized egg becomes implanted in the uterine wall.

As used herein, the menstrual fluid contains cervical mucus, vaginal discharge, uterine cells, uterine epithelial cells and capillary vessel blood and is mainly composed of proteins which form cells and the like. Herein, the uterine epithelial cells shed from the uterus and contained in menstrual fluid are referred to as "the decidua of menstrual fluid".

The adipose-derived stem cells are obtained from adipose tissue harvested through liposuction, and grow attached to plastic.

As described above, the placental decidua and the decidua of menstrual fluid are mainly composed of uterine epithelial cells. In Examples of the present invention, only the urinary incontinence therapeutic effect of the placental decidua-derived stem cells was specifically demonstrated, but it can be readily inferred that the stem cells derived from the decidua of menstrual fluid also have the effect of treating urinary incontinence. Moreover, the adipose-derived stem cells also have multipotentcy, and thus it can be readily inferred that the adipose-derived stem cells can be used to treat urinary incontinence. Therefore, it will be obvious to a person skilled in the art that the present invention makes it possible to realize not only a cellular therapeutic agent for treating urinary incontinence containing placental decidua-derived stem cells, but also a cellular therapeutic agent for treating urinary incontinence containing stem cells derived from the decidua of menstrual fluid or stem cells derived from adipose.

EXAMPLES

Hereinafter, the present invention will be described in further detail with reference to examples. It is to be understood, however, that these examples are for illustrative purposes only and are not to be construed to limit the scope of the present invention.

Example 1

Isolation and Culture of Stem Cells According to the Present Invention (1) Isolation and Culture of Placental Decidua-Derived Stem Cells The decidua was isolated from the placenta in the following manner according to the method described in Korean Patent Publication No. 10-2007-0101756A filed in the name of the applicant. Specifically, the placentas were collected from normal births and premature births in Guro Hospital, Korea University Medical Center, according to the Institutional Review Board Guidelines of Korea University Medical Center and used for research purposes. The placenta tissues were transferred to the laboratory in a state in which it was contained in physiological saline containing an antibiotic. The placenta tissues transferred to the laboratory were washed with PBS to remove blood cells and various other tissues, or the tissues were treated with hemolysis buffer to remove blood cells, or each of amnion, chorion, decidua and placental bed tissues constituting the placenta was carefully isolated using forceps.

Each of the isolated decidua tissues was placed on a 100-mm dish and finely cut with a sterilized scissor to a size of 1-2 mm. Then, the cut tissue was placed in a collagenase-containing medium and was incubated in an incubator at 37° C. for 1-4 hours, after which the tissues treated with collagenase were filtered through 100-mesh wire cloth. The cells thus isolated were placed in a 75-flask and cultured in a bFGF-containing DMEM at 37° C. in a condition of 5% $CO_2$ (FIG. 1).

(2) Isolation and Culture of Adipose-Derived Stem Cells

Adipose-derived stem cells used in this Example were adipose-derived stem cells isolated according to the method described in Korean Patent Registration No. 10-0679642 filed in the name of the applicant. Specifically, adipose tissue was isolated from the abdominal region by suction lipectomy and washed with PBS and then finely cut. The cut tissue was digested in collagenase type 1 (1 mg/ml)-containing DMEM, at 37° C. for 2 hours. The digested tissue was washed with PBS and then centrifuged at 1000 rpm for 5 minutes. The supernatant was suctioned off, and the pellets remaining on the bottom were washed with PBS and then centrifuged at 1000 rpm for 5 minutes. The resulting pellets were filtered through a 100 μm mesh to remove debris, followed by washing with PBS. The resulting cells were incubated in a DMEM medium (10% FBS, 2 mM NAC, 0.2 mM ascorbic acid). After overnight, unattached cells were washed with PBS, and cultured in Keratinocyte-SFM media (containing 2 mM NAC, 0.2 mM ascorbic acid, 0.09 mM calcium, 5 ng/ml rEGF, 50 BPE, 5 μg/ml insulin and 74 ng/ml hydrocortisone) while the media were replaced at two-day intervals, thus isolating multipotent stem cells.

Example 2

Examination of Proliferation Rate of Placental Decidua-Derived Stem Cells

The proliferation rate of the stem cells obtained according to the above-described method of proliferating the human placental decidua tissue-derived multipotent stem cells, was examined. Placental decidua-derived stem cells resulting from the placental decidua tissue samples of different human individuals were obtained through the isolation method described in Example 1, and then seeded into a 75-flask at a density of $2 \times 10^5$ cells.

CPDL is an index indicative of the proliferation rate of cells and expressed as the following equation:

$$CPDL = \ln(Nf/Ni)/\ln 2$$

wherein, Ni: the initial number of seeded cells; and Nf: the final number of cells.

The CPDL of the decidua-derived stem cells and was observed according to passage number and, as a result, the cells showed a CPDL value of about 30 at passage 12. This CPDL value was similar to that of human adipose tissue-derived stem cells (Lin et al., stem cells and development, 14:92, 2005; Zuk et al., *Tissue eng.*, 7:211, 2001). These results suggest that the placental decidua-derived stem cells according to the present invention have very high proliferation rate (FIG. 2).

Example 3

Immunological Characteristics of Placental Decidua-Derived Multipotent Stem Cells The placental decidua-derived multipotent stem cells obtained in Example 1 were washed with PBS and treated with trypsin. Then, the cells were collected and centrifuged at 1000 rpm for 5 minutes. After the supernatant was discarded, the cells were suspended in PBS and dispensed into each well at a cell density of $1 \times 10^5$ cells. An antibody (R-phycoerythrin-conjugated mouse anti-human monoclonal antibody) was placed into each well, and the cells were incubated at 4° C. for 40 minutes. After the incubation, the cell broth was centrifuged at 1000 rpm for 5 minutes. After the supernatant was removed, the cells were washed with PBS and centrifuged at 1000 rpm for 5 minutes. Then, after the supernatant was removed, the cells were washed with PBS and centrifuged at 1500 rpm for 5 minutes. After the supernatant was removed, the cells were fixed with 1% paraformaldehyde and analyzed using a flow cytometer. As a result of analysis, the immunological characteristics of the placental decidua-derived stem cells according to the present invention, as can be seen in Table 1, the cells showed immunophenotypes positive for CD29, CD90, Oct-4, SSEA-4 and Cripto-1, but negative for CD31 and CD45 (FIG. 4).

TABLE 1

| Surface antigen analysis (FACS analysis) of placental decidua-derived stem cells | |
|---|---|
| Antigen | Decidua-MSCs |
| CD29 | + |
| CD31 | − |
| CD45 | − |
| CD90 | + |
| Oct-4 | + |
| SSEA-4 | + |
| Cripto-1 | + |

Example 4

Analysis of Oct4 and SSEA-4 Expression of Placental Decidua-Derived Multipotent Stem Cells The placental decidua-derived stem cells obtained in Example 1 were washed three times with PBS and fixed with 4% paraformaldehyde-containing PBS for 30 minutes. After washing three times with PBS, the cells were permeabilized with 0.1% Triton-X100-containing PBS for 10 minutes. After washing three times with PBS, the cells were treated with blocking buffer (5% goat serum) and incubated at 4° C. for one hour, and then allowed to react with a primary antibody-containing blocking buffer overnight. After washing three times with PBS, the cells were allowed to react with a secondary antibody in a dark room for 1 hour.

After washing three times with PBS, the cells were mounted. As a result, as shown in FIG. 5, the multipotent stem cells according to the present invention were positive for Oct4 and SSEA-4 that are markers for human embryonic stem cells.

Also, the expression of Oct4 was analyzed using RT-PCR. The RT reaction was performed for 50 minutes at 37° C. and 10 minutes at 70° C., and the PCR reaction was performed for 5 minutes at 95° C., and 40 cycles, each consisting of 30 sec at 95° C., 40 sec at 58° C. and 1 min at 72° C., and then 10 minutes at 72° C. As a result, as shown in FIG. 6, it could be seen that the decidua-derived stem cells were expressed at 800 bp.

Example 5

Differentiation of Placental Decidua-Derived Multipotent Stem Cells into Myocytes The placental decidua-derived multipotent stem cells obtained in Example 1 were dispensed into a 10 ng/ml fibronectin-coated flask, and then pretreated with 10 μM 5'-azacytidine for 24 hours. After the pretreatment, the cells were cultured in SKBM (Cambrex, Co.) for 10 days, followed by immunostaining.

Figure 7:
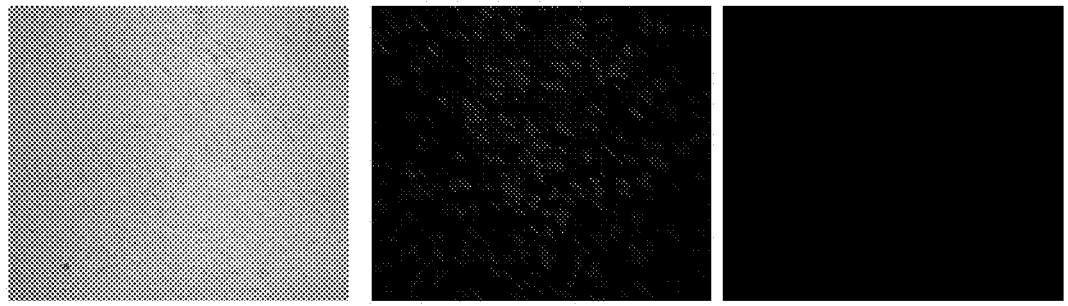
FIG. 7 is a microscopic photograph showing the results of immunocytochemical analysis (αMyosin-FITC) for decidua-derived stem cells induced for 10 days in MM-3160 medium (SKBM medium for myogenic differentiation) in myogenesis.
Figure 7:
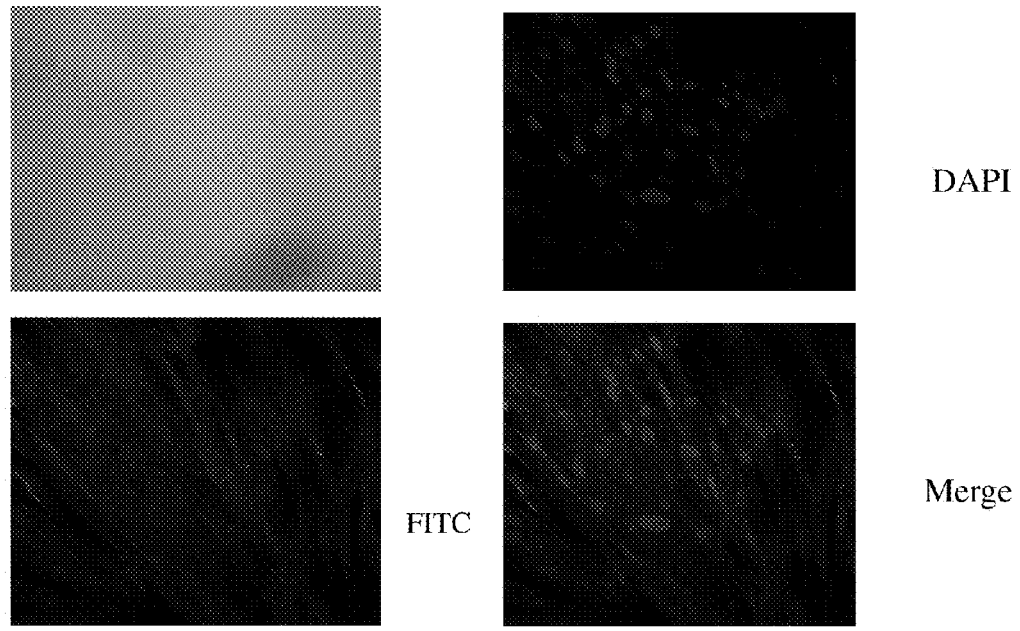

As a result, the placenta tissue-derived multipotent stem cells according to the present invention were positive for myosin that is a muscle cell-specific antigen. This result suggests that the human placenta tissue-derived multipotent stem cells according to the present invention differentiated into myocytes (FIG. 7).

Example 6

Measurement of Leak Point Pressure in Female Nude Mice Injected with Placental Decidua-Derived Stem Cells (1) Preparation of Experimental Animal Model In order to measure the effect of the placental decidua-derived stem cells on leak point pressure, 56 female nude mice were used. The female nude mice were divided into a normal group (n=14), a control group (n=14; in which the pudendal nerve was cut), experimental group 1 (n=14; injected with $10^5$ placental decidua-derived stem cells 2 weeks after the pudendal nerve was cut), and experimental group 2 (n=14; injected with $10^7$ placental decidua-derived stem cells 2 weeks after the pudendal nerve was cut). Each of the groups was subdivided into a 4-week group (n=7) and a 8-week group (n=7) and measured for leak point pressure at 4 weeks and 8 weeks.

Preparation of control group: 14 female nude mice were anesthetized with halothane, and the ischiorectal fossa was dissected bilaterally to transect the pudendal nerve. Then, the pudendal nerve was electrocauterized by about 2 cm, and then the skin was sutured.

Figure 8:
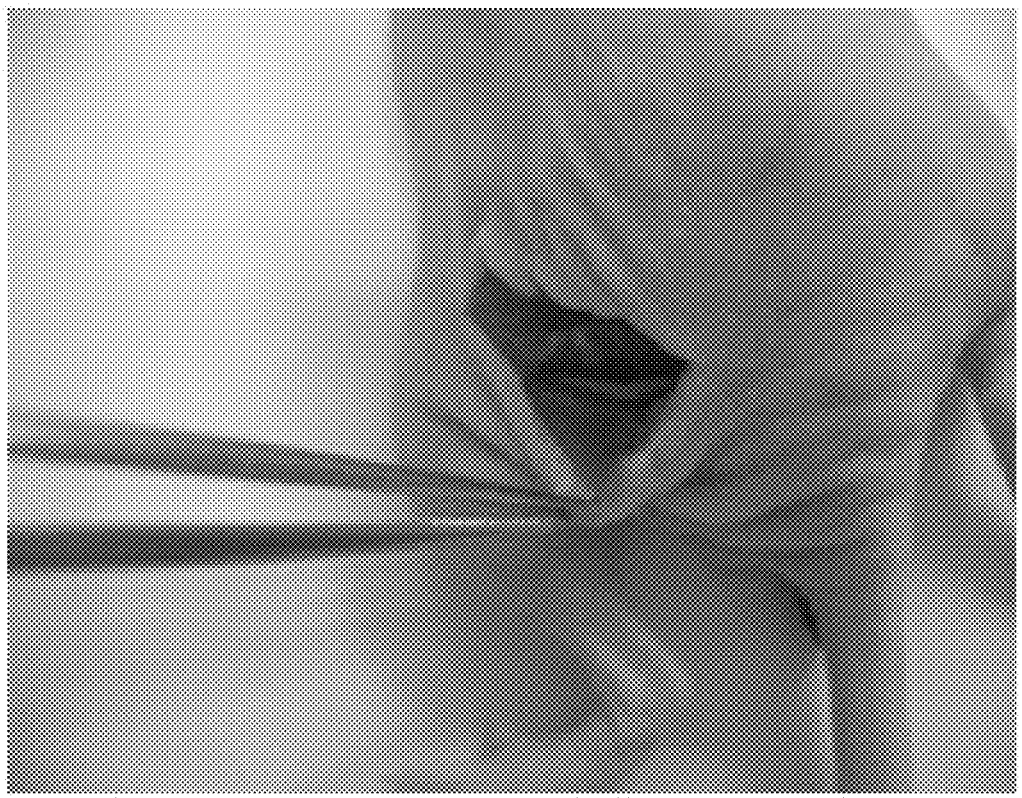
FIG. 8 is a photograph showing that the pudendal nerve of a nude mouse is transected.

Preparation of experimental groups 1 and 2: 28 female nude mice were anesthetized with halothane, the abdomen was opened by a low midline incision, and then the bladder and the urethra were detached (FIG. 8). After urinary incontinence occurred 2 weeks after the pudendal nerve transection, $10^5$ placental decidua-derived stem cells obtained in Example 1 were injected into 14 mice by a 10-ml Hamilton syringe using a microscope (experimental group 1), and the other 14 mice were injected with $10^7$ cells (experimental group 2).

(2) Measurement of Leak Point Pressure

The female nude mice were anesthetized with urethane (1.2 g/kg), and the spinal cord was transected at the level of T9-T10. Then, the abdomen was opened by low midline incision to detach the bladder, and then the bladder was subjected to suprapubic cystostomy using a PE-90 catheter.

Figure 9:
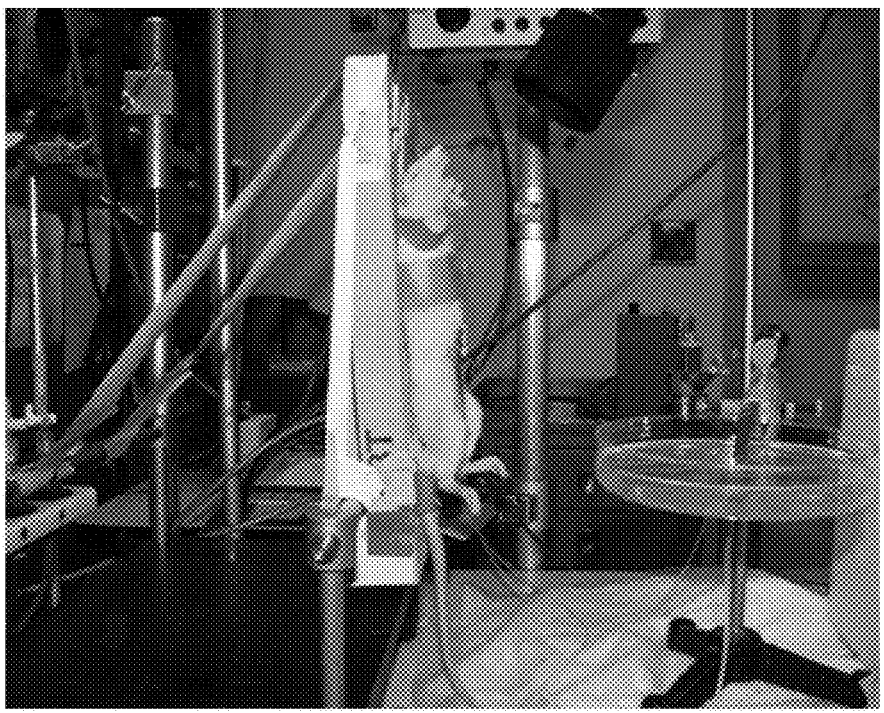
FIG. 9 is a photograph showing a process of measuring leak point pressure using a tilt table (A and B).
Figure 9:
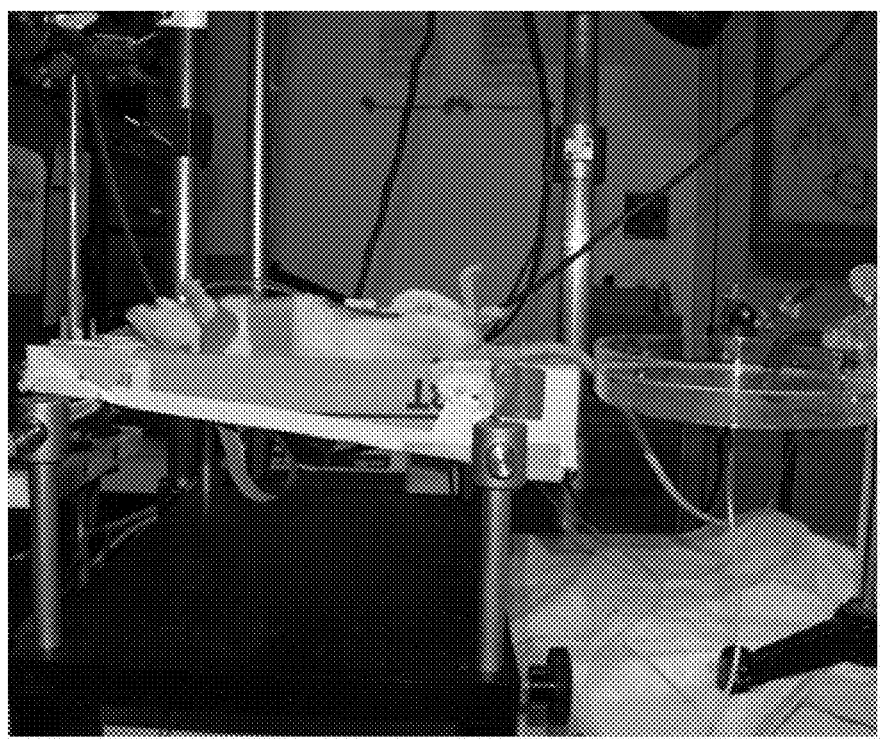

For the measurement of leak point pressure, the female nude mice of each of the normal group, the control group and the experimental groups were placed in the vertical tilt/intraversical pressure clamp model (FIG. 9). 150 ml of physiological saline was connected to a PE-90 tube, and the height of the saline was increased slightly each time to increase the intravesical pressure of the experimental mice. The pressure recorded at the beginning of leakage of urine was defined as LPP (leak point pressure).

Figure 10:
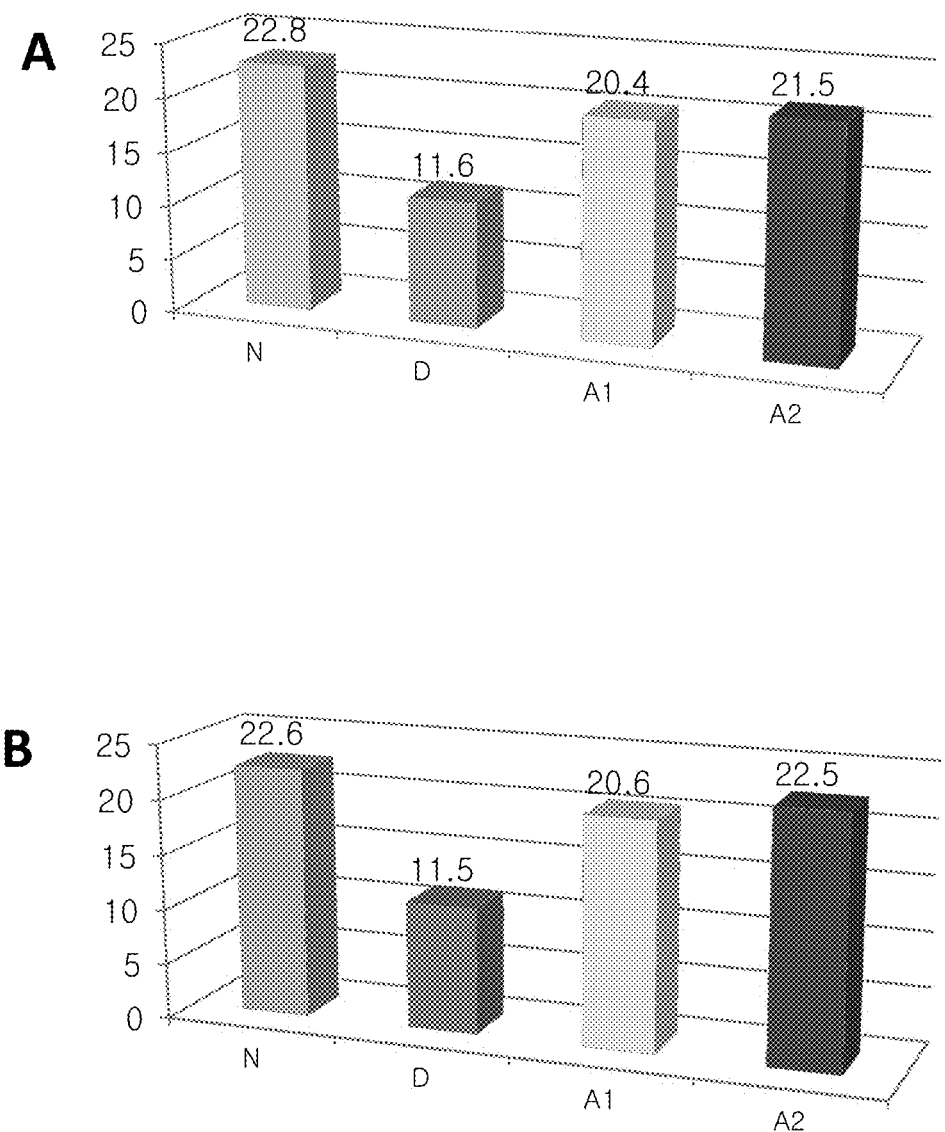
FIG. 10 is a graphic diagram showing the results of leak point pressure measured according to the results obtained in Example 6 (A: leak point pressure at 4 weeks, B: leak point pressure at 8 weeks, N: normal group, D: control group, P1: experimental group 1, and P2: experimental group 2).

As shown in FIG. 10, the normal group (N), the control group (D), the experimental group 1 (P1) and the experimental group 2 (P2) showed leak point pressures of 22.8±0.9, 11.6±0.6, 20.4±0.8 and 21.5±0.9 cmH$_2$O, respectively, at 4 weeks (FIG. 10A), and showed leak point pressures of 22.6±0.8, 11.5±0.7, 20.6±0.6 and 22.5±0.8 cmH$_2$O, respectively, at 8 weeks (FIG. 10B). Thus, at both 4 weeks and 8 weeks, the leak point pressures of the normal group and the experimental groups 1 and 2 were statistically higher than that of the control group, and the leak point pressure of the control group was lower than that of the normal group. Thus, in the experimental groups 1 and 2 administered with the placental decidua-derived stem cells prepared in Example 1, the leak point pressures were increased to a level similar to that of the normal group, suggesting that the placental deciduas-derived stem cells functioned to increase the leak point pressure.

Example 7

Measurement of Leak Point Pressure in Female Nude Mice Injected with Adipose-Derived Stem Cells (1) Preparation of Experimental Animal Model In order to measure the effect of the adipose-derived stem cells on leak point pressure, 56 female nude mice were used. The female nude mice were divided into a normal group (n=14), a control group (n=14; in which the pudendal nerve was cut), experimental group 1 (n=14; injected with $10^5$ adipose-derived stem cells 2 weeks after the pudendal nerve was cut), and experimental group 2 (n=14; injected with $10^7$ adipose-derived stem cells 2 weeks after the pudendal nerve was cut). Each of the groups was subdivided into a 4-week group (n=7) and a 8-week group (n=7) and measured for leak point pressure at 4 weeks and 8 weeks.

Preparation of control group: 14 female nude mice were anesthetized with halothane, and the ischiorectal fossa was dissected bilaterally to transect the pudendal nerve. Then, the pudendal nerve was electrocauterized by about 2 cm, and then the skin was sutured.

Preparation of experimental groups 1 and 2: 28 female nude mice were anesthetized with halothane, the abdomen was opened by low midline incision, and then the bladder and the urethra were detached (FIG. 8). After urinary incontinence occurred 2 weeks after the pudendal nerve transection, $10^5$ adipose-derived stem cells obtained in Example 1 were injected into 14 mice by a 10-ml Hamilton syringe using a microscope (experimental group 1), and the other 14 mice were injected with $10^7$ cells (experimental group 2).

(2) Measurement of Leak Point Pressure

Female nude mice were anesthetized with urethane (1.2 g/kg), and the spinal cord was transected at the level of T9-T10. Then, the abdomen was opened by low midline incision to detach the bladder, and then the bladder was subjected to suprapubic cystostomy using a PE-90 catheter.

For the measurement of leak point pressure, the female nude mice of each of the normal group, the control group and the experimental groups were placed in the vertical tilt/intraversical pressure clamp model (FIG. 9). 150 ml of physiological saline was connected to a PE-90 tube, and the height of the saline was increased slightly each time to increase the intravesical pressure of the experimental mice.

The pressure recorded at the beginning of leakage of urine was defined as LPP (leak point pressure).

Figure 11:
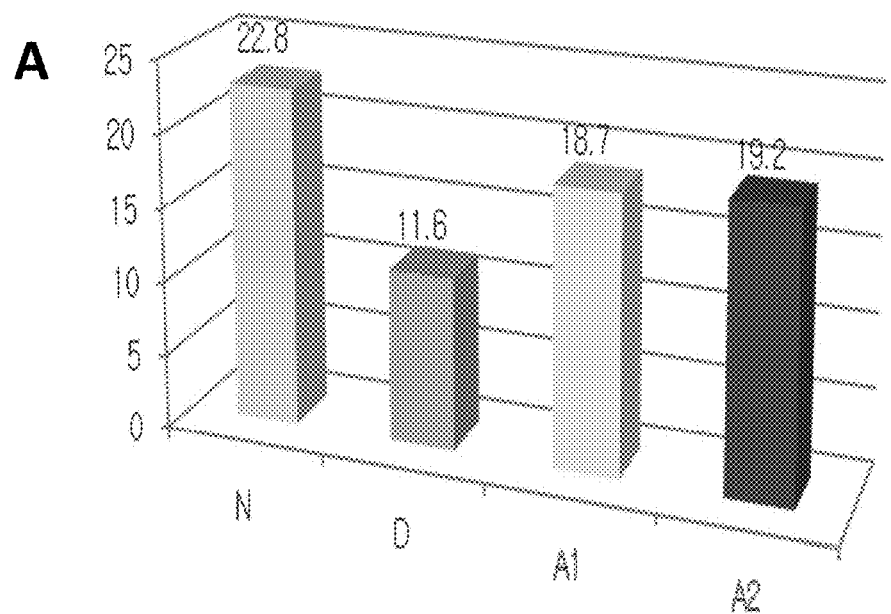
FIG. 11 is a graphic diagram showing the results of leak point pressure measured according to the results obtained in Example 7 (A: leak point pressure at 4 weeks, B: leak point pressure at 8 weeks, N: normal group, D: control group, A1: experimental group 1, and A2: experimental group 2).
Figure 11:
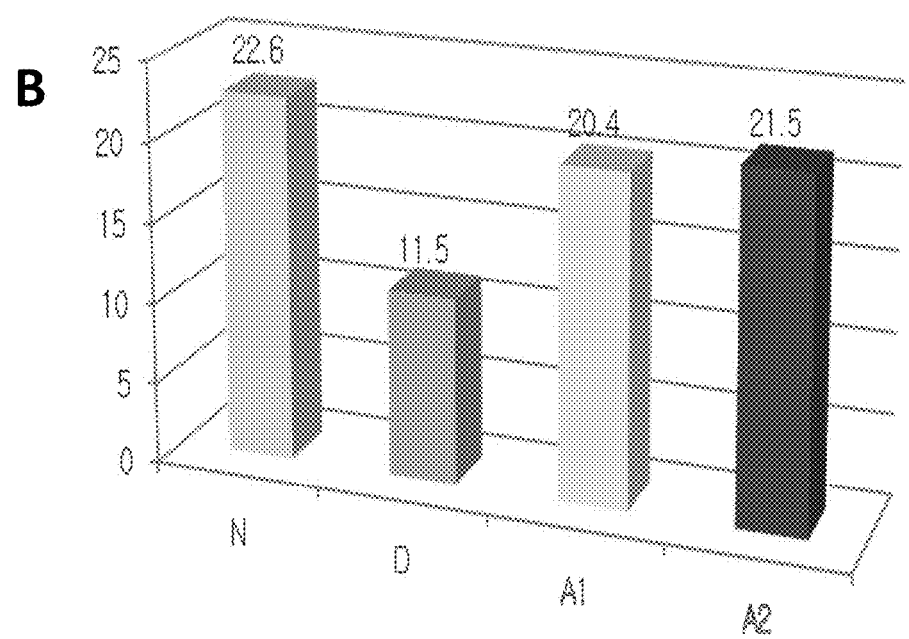

As shown in FIG. 11, the leak point pressures of the normal group (N), the control group (D), the experimental group 1 (A1) and the experimental group 2 (A2) were 22.8±0.9, 11.6±0.7, 18.7±0.9 and 19.2±0.7 cmH$_2$O, respectively, at 4 weeks ("A" of FIG. 11), and were shown to be 22.6±0.9, 11.5±0.7, 20.4±0.7 and 21.5±0.8 cmH$_2$O, respectively, at 8 weeks ("B" of FIG. 11). Thus, it could be confirmed that, in the experimental groups A1 and A2 administered with the adipose-derived stem cells of the present invention, the leak point pressure was increased at both 4 weeks and 8 weeks. Also, the leak point pressure of the group A2 was higher than that of the group A1, but there was no statistical difference therebetween (FIG. 11).

Example 8

Measurement of Urethral Sphincter Contractility in Male Mice Injected With Placental Decidua-Derived Stem Cells (1) Preparation of Experimental Animal Model In order to measure the influence of the placental decidua-derived stem cells on urethral sphincter contractility, 56 male mice were used. The male mice were divided into a normal group (n=14), a control group (n=14; in which the pudendal nerve was transected), experimental group 1 (n=14; injected with $10^5$ placental decidua-derived stem cells 2 weeks after the pudendal nerve was cut), and experimental group 2 (n=14; injected with $10^7$ placental decidua-derived stem cells 2 weeks after the pudendal nerve was cut). Each of the groups was subdivided into a 4-week group (n=7) and a 8-week group (n=7) and measured for urethral sphincter contractility at 4 weeks and 8 weeks.

Preparation of control group: 14 male mice were anesthetized with halothane, and the ischiorectal fossa was dissected bilaterally to transect the pudendal nerve. Then, the pudendal nerve was electrocauterized by about 2 cm, and then the skin was sutured.

Preparation of experimental groups 1 and 2: 28 male mice were anesthetized with halothane, the abdomen region was opened by low midline incision, and then the bladder and the urethra were transected (FIG. 8). After urinary incontinence occurred 2 weeks after the pudendal nerve transection, $10^5$ placental decidua-derived stem cells obtained in Example 2 were injected into 14 mice by a 10-ml Hamilton syringe using a microscope (experimental group 1), and the other 14 mice were injected with $10^7$ cells (experimental group 2).

(2) Measurement of Urethral Sphincter Contractility

Figure 12:
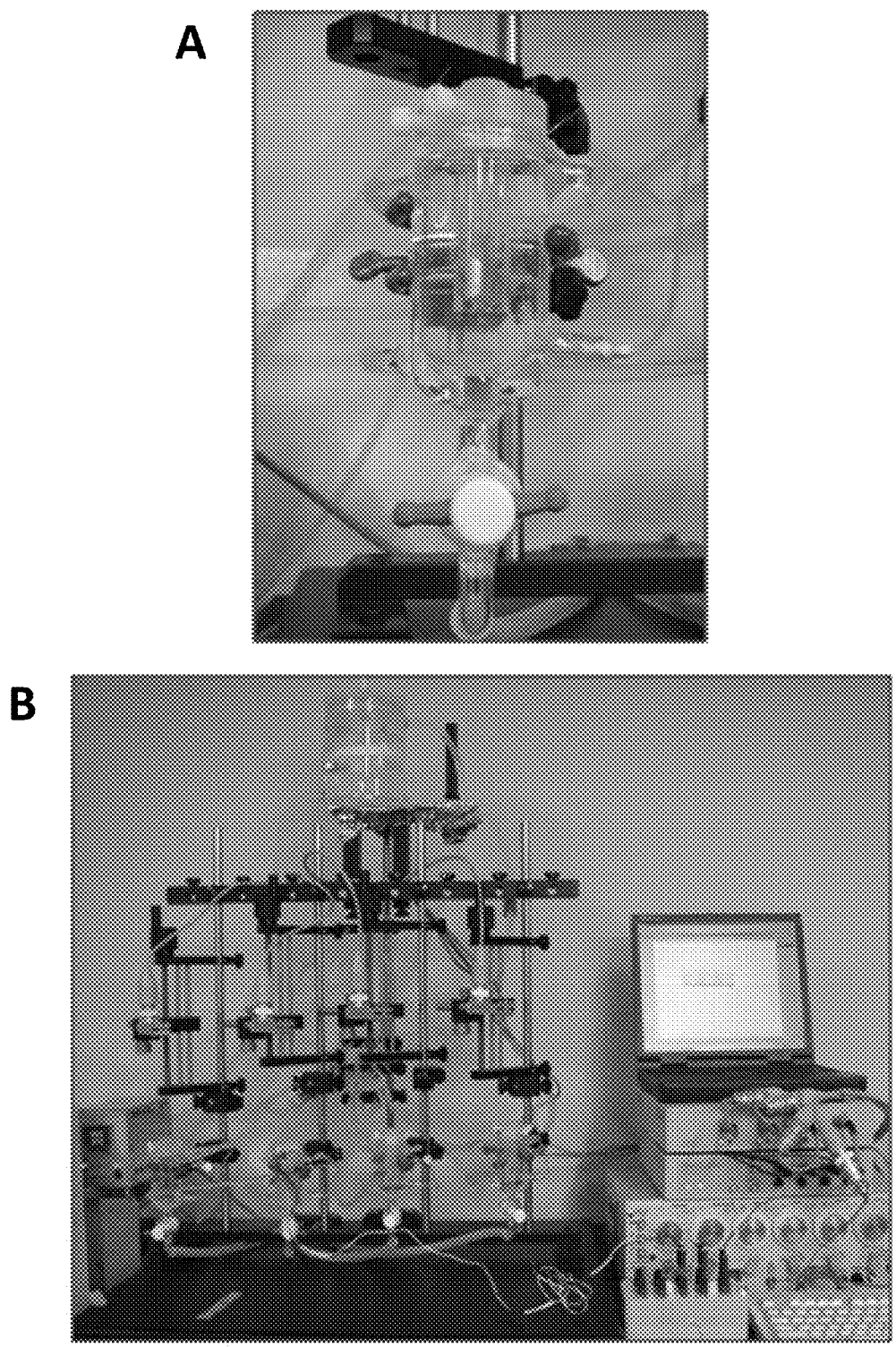
FIG. 12 is a photograph showing a process of measuring urethral sphincter contractility using an organ bath (A and B).

After the urethra of each of the male mice was obtained, the urethra was spirally cut, thus preparing urethral tissue sections (10×2 mm). In an organ bath experiment, a vertical chamber (20-ml volume) was perfused with $CO_2$/bicarbonate buffered Tyrode solution, and then the urethral tissue sections were fixed in the chamber. Then, the urethral sphincter contractility in the urethral tissue sections was examined using acetylcholine (FIG. 12).

Figure 13:
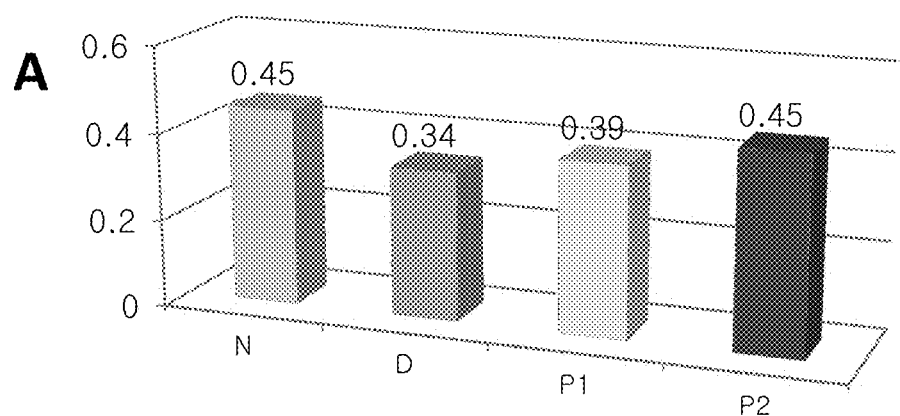
FIG. 13 is a graphic diagram showing the urethral sphincter contractility measured by electrical field stimulation, according to the results obtained in Example 8 (A: urethral sphincter contractility at 4 weeks; B: urethral sphincter contractility at 8 weeks; N: normal group; D: control group; P1: experimental group 1; and P2: experimental group 2).
Figure 13:
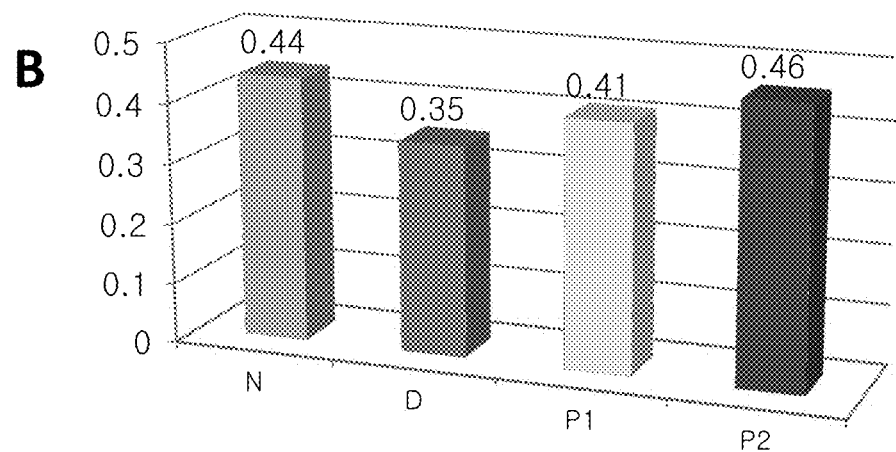

As a result, as shown in FIG. 13, when electrical field stimulation (EFS, 60V) which is conventionally used in the prior art was performed in the male mouse experiment, the urethral sphincter contraction values in the normal group (N), the control group (D), the experimental group 1 (P1) and the experimental group 2 (P2) were 0.45±0.06, 0.34±0.02, 0.39±0.02 and 0.45±0.05 g/tension, respectively, at 4 weeks, and were 0.44±0.06, 0.35±0.02, 0.41±0.04 and 0.46±0.03 g/tension, respectively, at 8 weeks. Accordingly, in the electrical field stimulation experiments, the experimental groups showed urethral sphincter contractility higher than that of the control group at both weeks and 8 weeks and showed urethral sphincter contractility similar to or higher than that of the normal group. In addition, the experimental group 2 showed urethral sphincter contractility higher than that of the experimental group 1.

Figure 14:
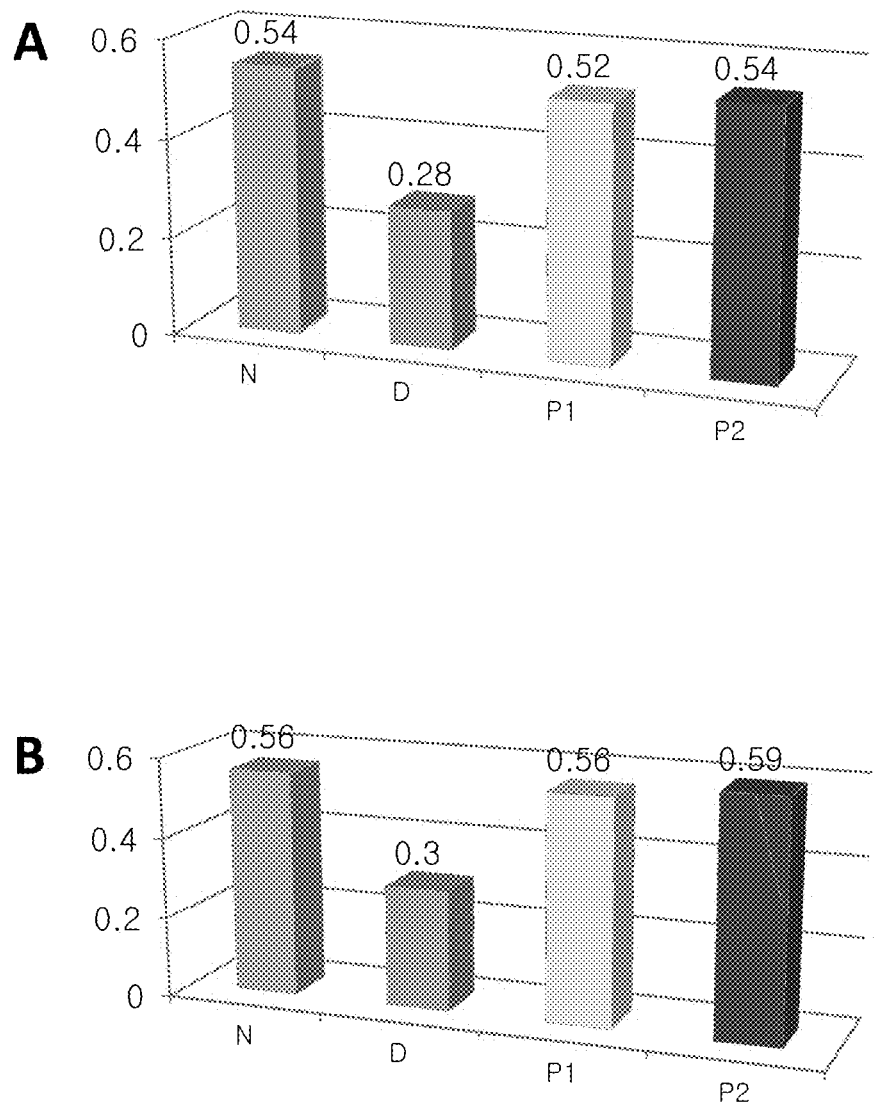
FIG. 14 is a graphic diagram showing the urethral sphincter contractility by measured administration of acetylcholine, according to the results obtained in Example 8 (A: urethral sphincter contractility at 4 weeks; B: urethral sphincter contractility at 8 weeks; N: normal group; D: control group; P1: experimental group 1; and P2: experimental group 2).

Meanwhile, as shown in FIG. 14, when the test samples were treated with acetylcholine (Ach), the urethral sphincter contraction values in the normal group (N), the control group (D), the experimental group 1 (P1) and the experimental group 2 (P2) were 0.54±0.04, 0.28±0.03, 0.52±0.02 and 0.54±0.03 g/tension, respectively, at weeks (FIG. 14A), and were 0.56±0.03, 0.3±0.02, 0.56±0.04 and 0.59±0.04 g/tension, respectively, at 8 weeks (FIG. 14B). Accordingly, when acetylcholine was administered, urethral sphincter contractility was higher in all the normal group and the experimental groups 1 and 2 than that in the group D, and the experimental group 2 showed urethral sphincter contractility higher than that of the experimental group 1, but there was no statistically significant difference therebetween. In other words, it cannot be concluded that the experimental group 2 shows urethral sphincter contractility higher than that of the experimental group 1.

Example 9

Measurement of Urethral Sphincter Contractility in Male Mice Administered with Adipose-Derived Stem Cells (1) Preparation of Experimental Animal Model In order to measure the influence of the adipose-derived stem cells on urethral sphincter contractility, 56 male mice were used. The male mice were divided into a normal group (n=14), a control group (n=14; in which the pudendal nerve was transected), experimental group 1 (n=14; injected with $10^5$ adipose-derived stem cells 2 weeks after the pudendal nerve was cut), and experimental group 2 (n=14; injected with $10^7$ adipose-derived stem cells 2 weeks after the pudendal nerve was cut). Each of the groups was subdivided into a 4-week group (n=7) and a 8-week group (n=7) and measured for urethral sphincter contractility at 4 weeks and 8 weeks.

Preparation of control group: 14 male mice were anesthetized with halothane, and the ischiorectal fossa was dissected bilaterally to transect the pudendal nerve. Then, the pudendal nerve was electrocauterized by about 2 cm, and then the skin was sutured.

Preparation of experimental groups 1 and 2: 28 male mice were anesthetized with halothane, the abdomen region was opened by low midline incision, and then the bladder and the urethra were transected (FIG. 8). After urinary incontinence occurred 2 weeks after the pudendal nerve transection, $10^5$ adipose-derived stem cells obtained in Example 1 were injected into 14 mice by a 10-ml Hamilton syringe using a microscope (experimental group 1), and the other 14 mice were injected with $10^7$ cells (experimental group 2).

(2) Measurement of Urethral Sphincter Contractility

After the urethra of each of the male mice was obtained, the urethra was spirally cut, thus preparing urethral tissue sections (10×2 mm). In an organ bath experiment, a vertical chamber (20-ml volume) was perfused with $CO_2$/bicarbonate buffered Tyrode solution, and then the urethral tissue sections were fixed in the chamber. Then, the urethral sphincter contractility in the urethral tissue sections was examined using acetylcholine (FIG. 12).

Figure 15:
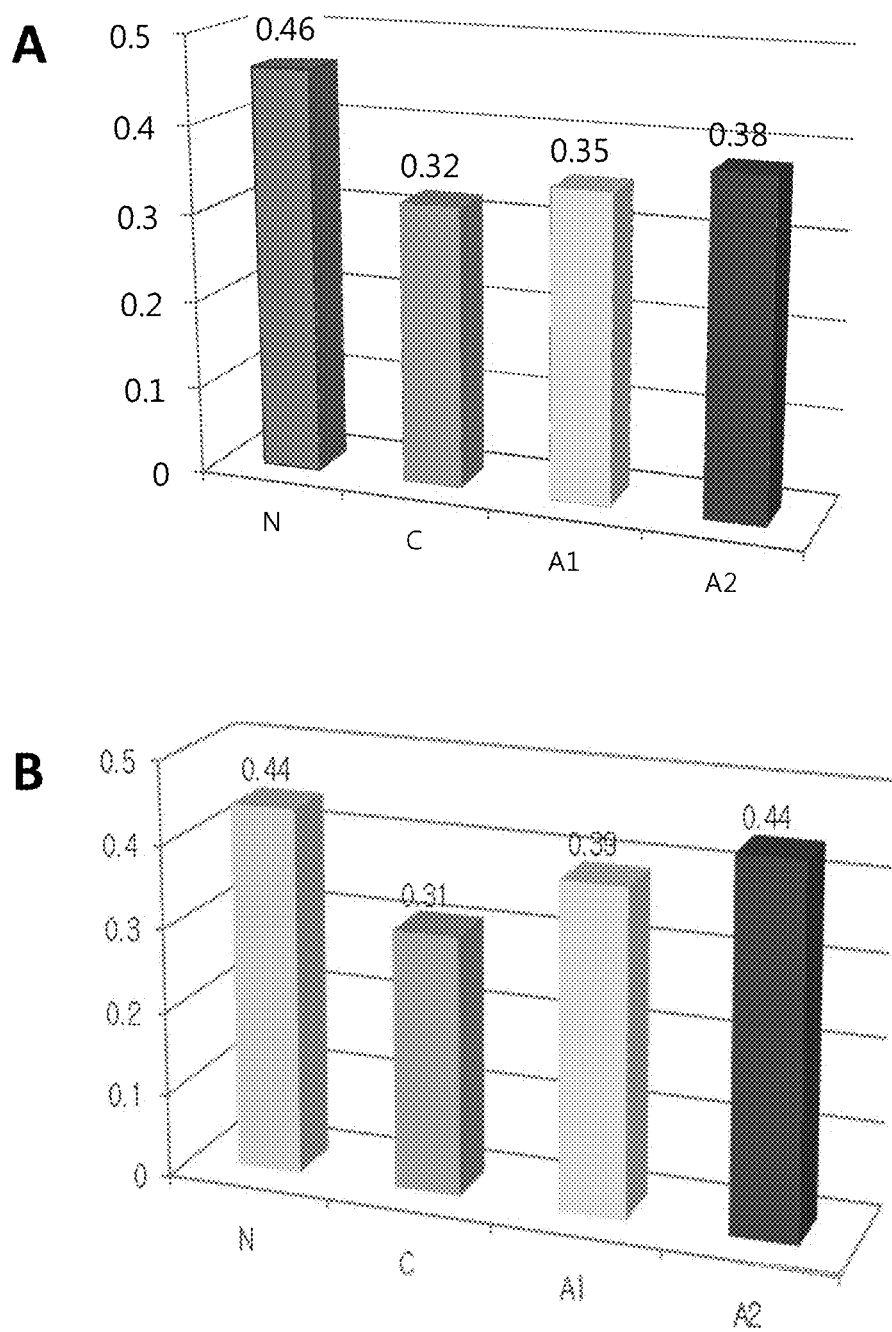
FIG. 15 is a graphic diagram showing the urethral sphincter contractility measured by electrical field stimulation, according to the results obtained in Example 9 (A: urethral sphincter contractility at 4 weeks; B: urethral sphincter contractility at 8 weeks; N: normal group; D: control group; A1: experimental group 1; and A2: experimental group 2).

As a result, as shown in FIG. 15, when electrical field stimulation (EFS, 60V) which is conventionally used in the prior art was performed in the male mouse experiment, the urethral sphincter contraction values in the normal group (N), the control group (D), the experimental group 1 (A1) and the experimental group 2 (A2) were 0.46±0.08, 0.32±0.03, 0.35±0.03 and 0.38±0.03 g/tension, respectively, at 4 weeks, and were 0.44±0.06, 0.31±0.02, 0.39±0.02 and 0.44±0.05 g/tension, respectively, at 8 weeks. Accordingly, in the electrical field stimulation experiments, urethral sphincter contractility was higher in the groups N and A than that in the group D at both weeks and 8 weeks and had no difference between the group A2 and the group A1.

Figure 16:
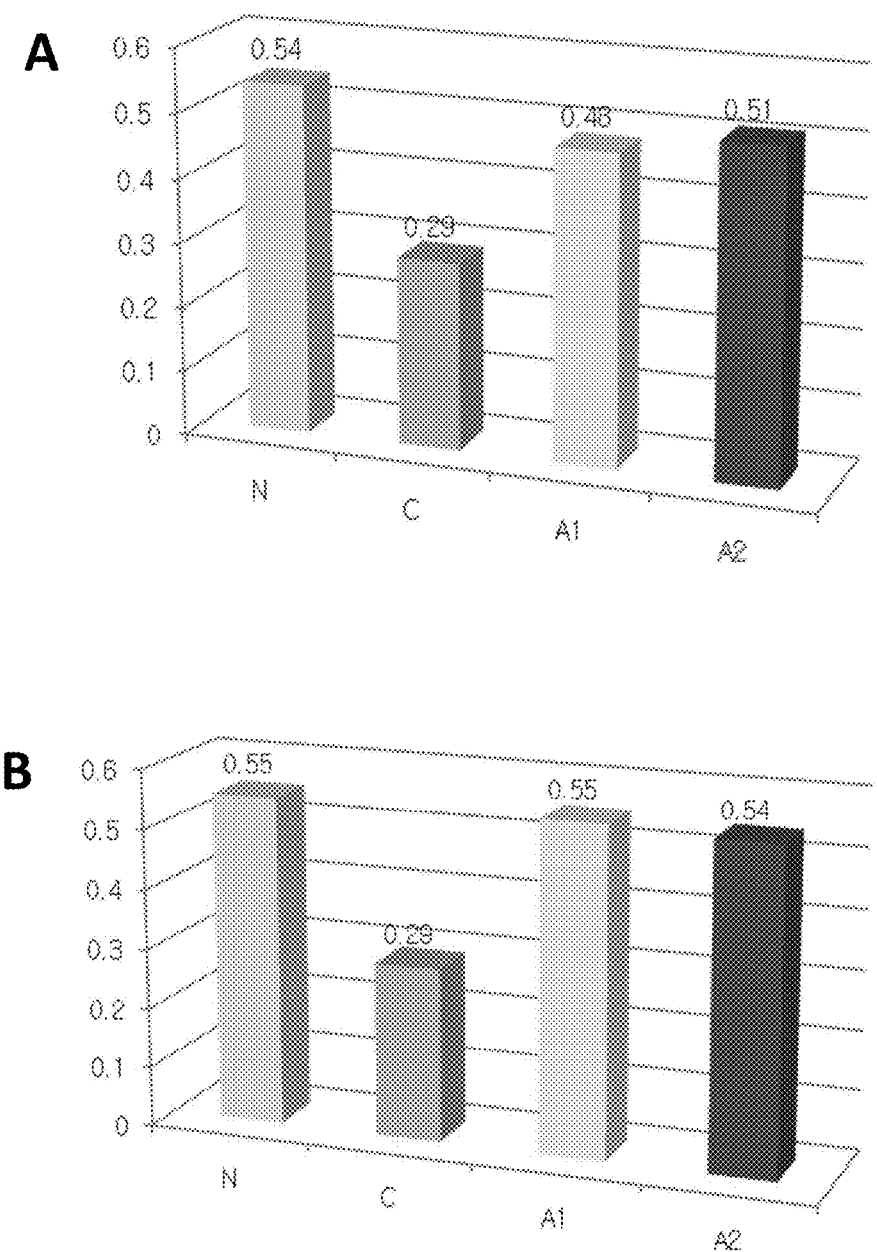
FIG. 16 is a graphic diagram showing the urethral sphincter contractility measured by the administration of acetylcholine, according to the results obtained in Example 9 (A: urethral sphincter contractility at 4 weeks; B: urethral sphincter contractility at 8 weeks; N: normal group; D: control group; A1: experimental group 1; and A2: experimental group 2).

Meanwhile, as shown in FIG. 16, when the test samples were administered with acetylcholine (Ach), the urethral sphincter contraction values in the normal group (N), the control group (D), the experimental group 1 (A1) and the experimental group 2 (A2) were 0.54±0.05, 0.29±0.04, 0.48±0.03 and 0.51±0.05 g/tension, respectively, at 4 weeks, and were 0.55±0.05, 0.29±0.03, 0.55±0.02 and 0.54±0.05 g/tension, respectively, at 8 weeks. Accordingly, when acetylcholine was administered, urethral sphincter contractility was higher in the normal group and the experimental groups 1 and 2 than that in the group D and had no difference between the group A2 and the group A1.

Example 10

Immunostaining of Mouse Tissue Injected with Placental Decidua-Derived Stem Cells After measuring leak point pressure and urethral sphincter contractility at 4 weeks and 8 weeks according to Examples 6 to 8 as described above, each of the urethral tissues was collected and frozen without damage using 2-methylbutane which has already been cooled in liquid nitrogen. The urethral tissues were cooled and sectioned, and then subjected to H/E staining. Also, in order to observe the differentiation of the stem cells into smooth muscles and skeletal muscles, the tissues were immunostained with DAPI, muscle actin (α-SMA) and myosin heavy chain (MyHC) and observed with a fluorescence microscope.

Figure 17:
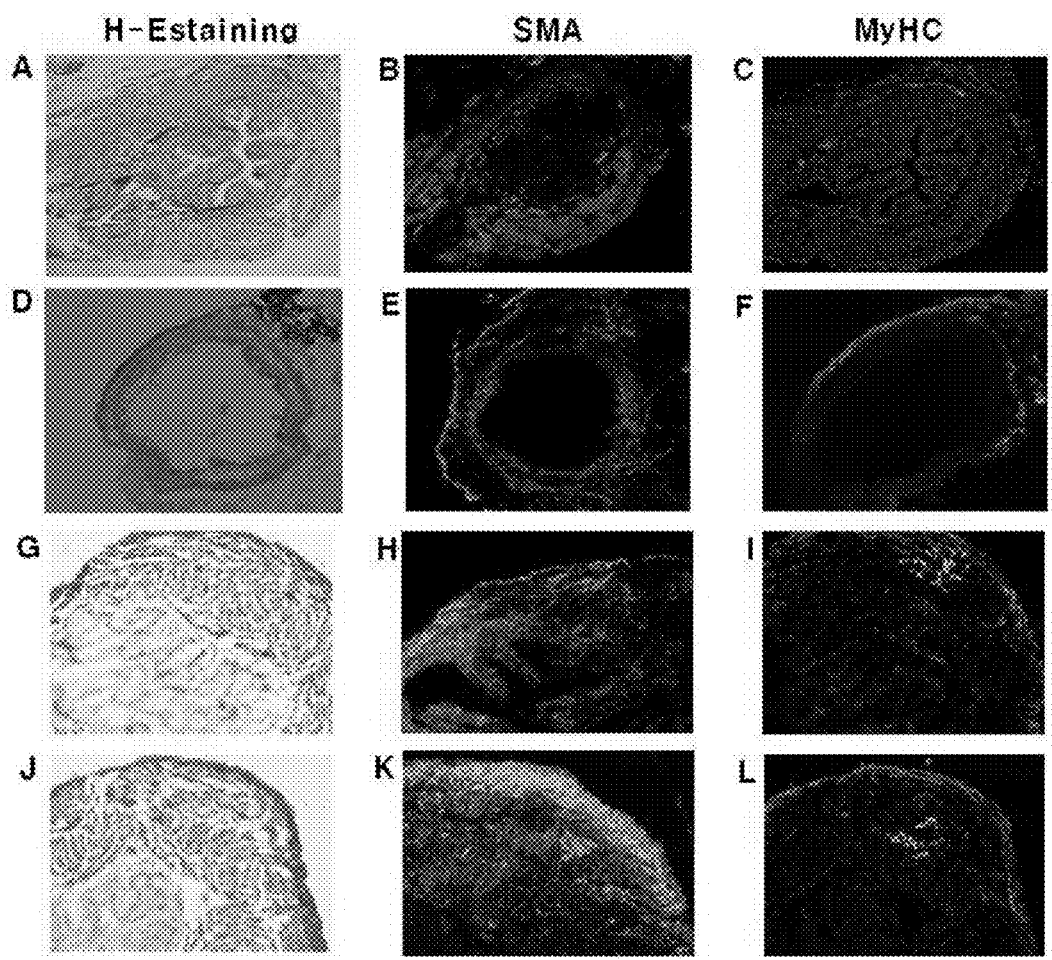
FIG. 17 shows the results of the H/E staining, SMA immunostaining and MyHC immunostaining of urethral tissue of female nude mice, conducted in Example 10.

As a result, as shown in FIG. 17, in the normal urethral sphincter muscles of the female nude mice according to Example 6, the smooth muscles were abundant, and the skeletal muscles were weakly stained ("A", "B" and "C" of FIG. 17). After the pudendal nerve transection, the reduction in the amount of smooth muscles was observed ("D", "E" and "F" of FIG. 17). When the placental decidua-derived stem cells were injected, at 4 weeks ("G", "H" and "I" of FIG. 17) and 8 weeks ("J", "K" and "L" of FIG. 17), the smooth muscles were stained with light green, suggesting that the amount of the smooth muscles was increased. Also, between the smooth muscles, yellow cells co-stained with red and green were observed. In the MyHC staining, the skeletal muscles were very weakly stained green, and the cells injected between the smooth cells showed red.

Figure 18:
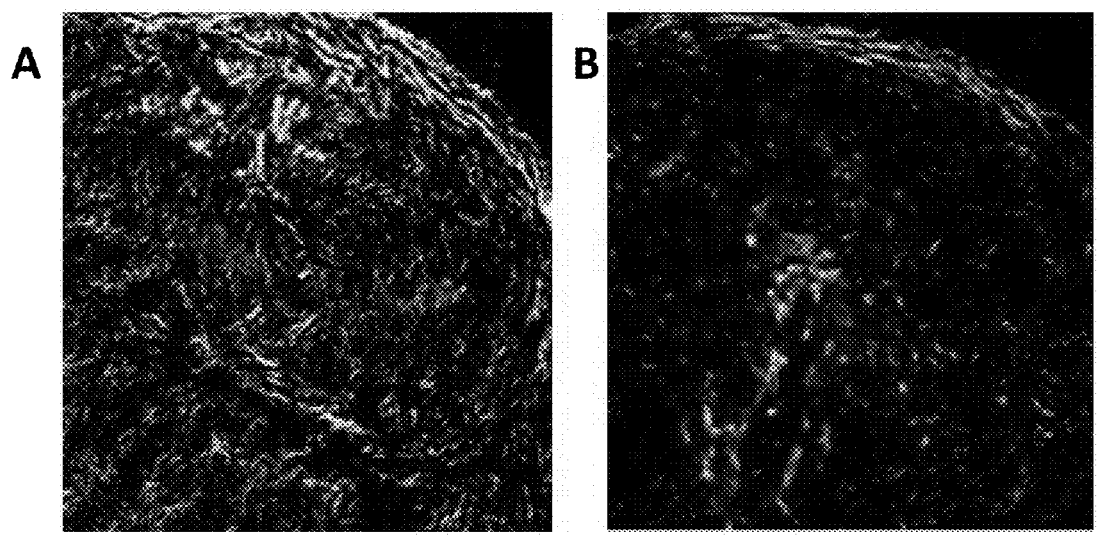
FIG. 18 shows the results of the H/E immunostaining of the urethral tissue of male mice, according to the results obtained in Example 10.

Also, as shown in FIG. 18, the original urethral shape could not be observed because the urethra of the male mice was spirally cut in Example 8 as described above; however, it was observed that PKH was expressed in the tissue after the experiment of urethral sphincter contractility ("A" and "B" of FIG. 18), suggesting that the injected placenta-derived stem cells contributed to urethral sphincter contraction. For reference, PKH is a substance for fluorescence staining of living cells, and in this Example, the placental decidua-derived stem cells were labeled with PKH (red) before injection.

In conclusion, in Examples 6 to 8 in which animal models of stress urinary incontinence, similar to urinary incontinence patients was constructed, the injection of the placental decidua-derived stein cells increased the leak point pressure in the nude mouse model of urinary incontinence and increased the urethral sphincter contractility in the mouse model of urinary incontinence. The leak point pressure did not greatly change according to the number of stem cells injected, but the urethral sphincter contractility increased as the number of injected stem cells increased. This suggests that the placental decidua-derived stem cells according to the present invention can also be used as excellent cellular therapeutic agents in urinary incontinence patients.

As mentioned above, the placental decidua and the decidua of menstrual fluid are mainly composed of uterine epithelial cells. In Examples of the present invention, only the urinary incontinence therapeutic effect of the placental decidua-derived stem cells was specifically demonstrated, but it can be readily inferred that the stem cells derived from the decidua of menstrual fluid also have the effect of treating urinary incontinence.

Example 11

Immunostaining of Mouse Tissue Injected with Adipose-Derived Stem Cells

After measuring leak point pressure and urethral sphincter contractility at 4 weeks and 8 weeks according to Examples 7 to 9 as described above, each of the urethral tissues was collected and frozen without damage using 2-methylbutane which has already been cooled in liquid nitrogen. The urethral tissues were cooled and sectioned, and then subjected to H/E staining. Also, in order to observe the differentiation of the stem cells into smooth muscles and skeletal muscles, the tissues were immunostained with DAPI, muscle actin (α-SMA) and myosin heavy chain (MyHC) and observed with a fluorescence microscope.

Figure 19:
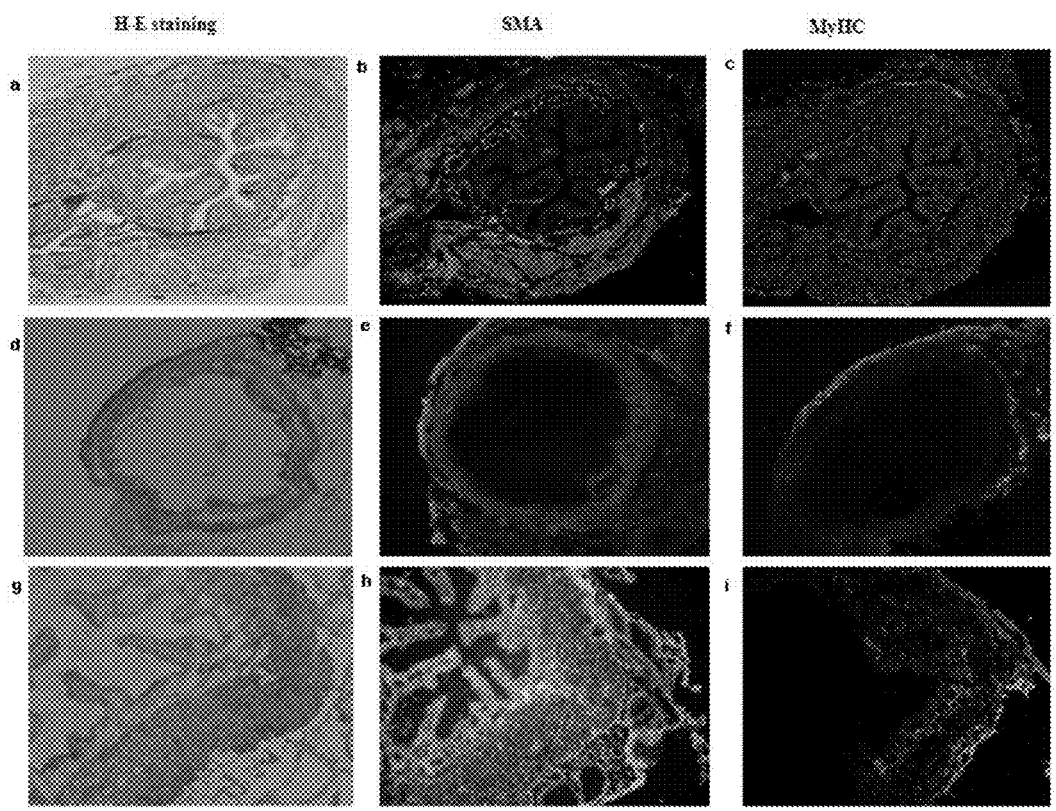
FIG. 19 shows the results of the H/E staining, SMA immunostaining and MyHC immunostaining of the urethral tissue of female nude mice, according to the results obtained in Example 11.

As a result, as shown in FIG. 19, in the normal urethral sphincter of the nude mice prepared in Example 7, the smooth muscles were abundant, and the skeletal muscles were weakly stained ("A", "B" and "C" of FIG. 19). After the pudendal nerve transection, the reduction in the amount of smooth muscles was observed ("D", "E" and "F" of FIG. 19). When adipose-derived stem cells were injected (at 8 weeks), the smooth muscles were stained with green, suggesting that the amount of the smooth muscles was increased. Also, between the smooth muscles, yellow cells co-stained with red and green were observed. In the MyHC staining, the skeletal muscles were very weakly stained, and the cells injected between the smooth cells showed red.

Figure 20:
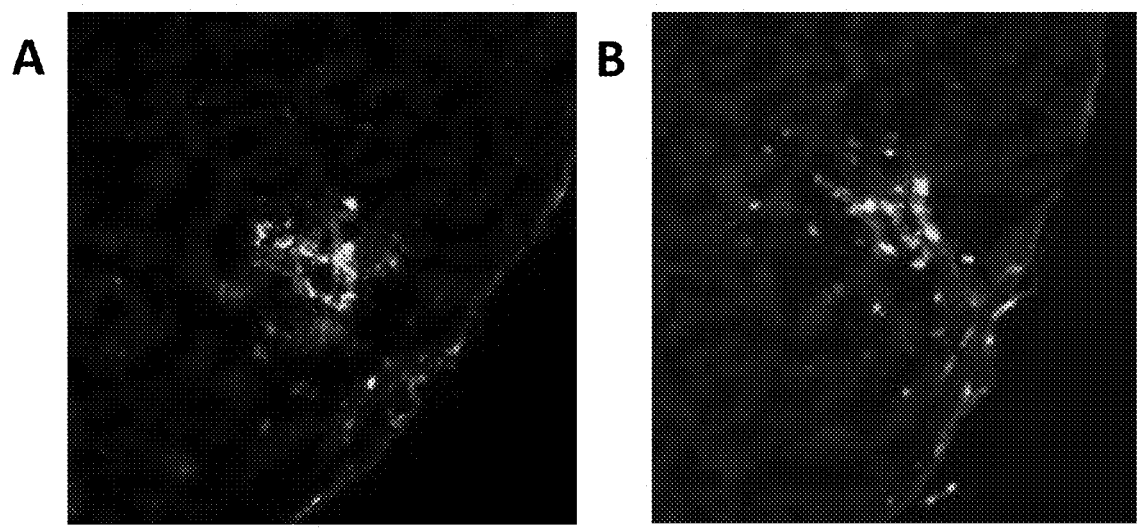
FIG. 20 shows the results of the H/E immunostaining of the urethral tissue of male mice, according to the results obtained in Example 11.

Also, as shown in FIG. 20, the original urethral shape could not be observed because the urethra of the male mice was spirally cut in Example 9 as described above; however, it was observed that PKH was expressed in the tissue after the experiment of urethral sphincter contractility (8 weeks; "A" and "B" of FIG. 20), suggesting that the injected adipose-derived stem cells contributed to urethral sphincter contraction. For reference, PKH is a substance for fluorescence staining of living cells, and in this Example, the adipose-derived stem cells were labeled with PKH (red) before injection.

INDUSTRIAL APPLICABILITY

As described above in detail, the stem cells derived from the decidua of the placenta or menstrual fluid or the stem cells derived from adipose according to the present invention have excellent ability to differentiate into myocytes, and thus show the effects of increasing leak point pressure and urethral sphincter contractility. Accordingly, the stem cells are useful as an agent for treating urinary incontinence.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:
1. A method for treating urinary incontinence in a patient in need thereof, said method comprising:
(i) obtaining tissue from the decidua of the placenta or the decidua of menstrual fluid and finely cutting the tissue;
(ii) digesting the finely cut tissue in medium containing collagenase, and then removing non-digested tissue;
(iii) centrifuging the digested tissues and then suspending the resulting pellets to obtain single cells;
(iv) culturing the single cells in a culture vessel in a medium containing bFGF, whereby stem cells attach to the culture vessel;
(v) collecting the attached stem cells;
(vi) formulating a cellular therapeutic agent comprising the stem cells; and
(vii) injecting the cellular therapeutic agent into the patient's lower abdominal region,
thereby increasing leak-point pressure,
wherein said stem cells have the following characteristics:
(a) positive for CD29 and CD90, but negative for CD31 and CD45;
(b) positive for Oct4, SSEA-4 and Cripto-1;
(c) ability to grow attached to plastic, showing morphological features of round or spindle shape, and forming spheres in serum-free medium so as to be able to be maintained in an undifferentiated state; and
(d) having the ability to differentiate into myocytes.

* * * * *